United States Patent [19]

Bigg et al.

[11] Patent Number: 5,385,931
[45] Date of Patent: Jan. 31, 1995

[54] SULFONAMIDES DERIVED FROM BENZOCYCLIC OR BENZOHETEROCYCLIC ACIDS, THEIR PREPARATION AND APPLICATION IN THERAPEUTICS

[75] Inventors: Dennis Bigg; Alain Duflos; Jean-Pierre Rieu, all of Castres, France

[73] Assignee: Pierre Fabre Medicament, Paris, France

[21] Appl. No.: 613,842

[22] PCT Filed: Apr. 4, 1990

[86] PCT No.: PCT/FR90/00234
§ 371 Date: Dec. 28, 1990
§ 102(e) Date: Dec. 28, 1990

[87] PCT Pub. No.: WO90/12007
PCT Pub. Date: Oct. 18, 1990

[30] Foreign Application Priority Data

Apr. 5, 1989 [FR] France .................. 89 04470

[51] Int. Cl.$^6$ .................. A61K 31/34; A61K 31/38; C07D 307/81; C07D 333/60
[52] U.S. Cl. .................. 514/443; 514/456; 514/465; 514/469; 514/555; 514/562; 514/530; 514/538; 549/51; 549/57; 549/409; 549/405; 549/436; 549/467; 560/10; 560/12; 560/13; 560/16; 562/430
[58] Field of Search .................. 549/51, 57, 467, 484, 549/405, 436; 514/443, 456, 469, 465, 555, 562, 530, 538; 562/430; 560/10, 12, 13, 16

[56] References Cited

U.S. PATENT DOCUMENTS

| | | | |
|---|---|---|---|
| 4,866,196 | 9/1989 | Iwakuma et al. | 560/12 |
| 4,918,809 | 8/1990 | Witte et al. | 560/12 |
| 4,929,754 | 5/1990 | Nickl et al. | 560/16 |
| 4,931,462 | 6/1990 | Friebe et al. | 514/419 |

OTHER PUBLICATIONS

D. F. McClure, et al., *J. Org. Chem.*, "Chiral α-Amino Ketones from the Friedel-Crafts Reaction of Protected Amino Acids," 46(11), pp. 2431-2433, (1981).
J. March (I), "Advanced Organic Chemistry," 2nd ed., pp. 353-356, 363-365, and 369-370, McGraw Hill Cook Co., New York (1977).
J. March (II), "Advanced Organic Chemistry" 3rd ed. pp. 353-354, Joh Wiley & Sons, New York (1985).
J. March, "Advanced Organic Chemistry" 3rd ed., pp. 392-393, and 804-806 John Wiley & Sons, New York (1985).
W. Foye, "Principles of Medicinal Chemistry" 2nd ed. pp. 80-81, Lea & Febiger, Philadelphia (1981).

*Primary Examiner*—Richard L. Raymond
*Attorney, Agent, or Firm*—Dressler, Goldsmith, Shore & Milnamow, Ltd.

[57] ABSTRACT

The invention relates to new sulphonamide derivatives of benzo-cyclic or benzo-heterocyclic acids and their derivatives of general formula I

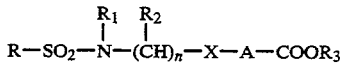

in which:
R represents a straight-chain or branched lower alkyl radical having 1 to 9 C;
a phenyl radical which is unsubstituted or substituted by one or more groups:
  straight-chain or branched lower alkyl having 1 to 4 C, halogeno, alkoxy, nitro, amino, dialkylamino or $CF_3$;
  a substituted or unsubstituted naphthalene;
  a thiophenyl radical;
$R_1$ represents a hydrogen or a straight-chain or branched lower alkyl or a benzyl;

(Abstract continued on next page.)

Abstract —continued $R_2$ represents a hydrogen, a straight-chain or branched lower alkyl group, a substituted or unsubstituted phenyl group or an aralkyl group;

$R_3$ represents a hydrogen or a straight-chain or branched lower alkyl (1 to 6 C);

—X— represents a divalent functional radical chosen from the following: —$CH_2$—;

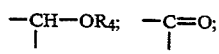

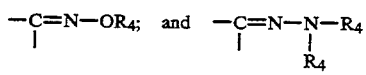

where $R_4$ = H or Me;

A represents a benzo-cyclic or benzo-heterocyclic divalent radical chosen from the following (a) to (j):

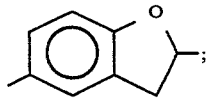 (a)

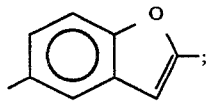 (b)

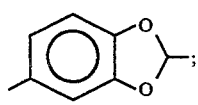 (c)

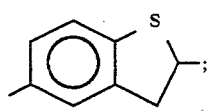 (d)

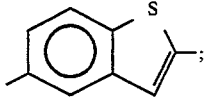 (e)

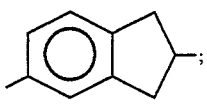 (f)

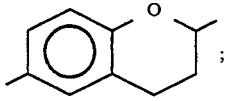 (g)

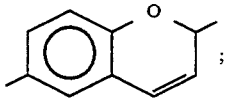 (h)

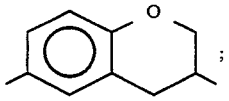 (i)

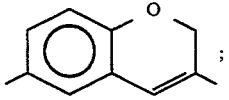 (j)

and n can assume the values 1 to 4 inclusive; and the therapeutically acceptable organic or inorganic salts ($R_3$=H), the pure isomers or diastereoisomers or their mixture and all the pharmaceutical compositions of formula I with other active principles.

The invention relates to the application of I as a medicament and the preparation processes.

33 Claims, No Drawings

SULFONAMIDES DERIVED FROM BENZOCYCLIC OR BENZOHETEROCYCLIC ACIDS, THEIR PREPARATION AND APPLICATION IN THERAPEUTICS

The present invention, made at the Centre de Recherche PIERRE FABRE (Pierre Fabre Research Center) relates to new sulphonamides, their preparation and their application as a medicament.

Platelet anti-aggregants—the essential activity of which is to combat thrombosis—are increasingly being used either for preventive purposes or as therapeutic adjuvants in this indication as well as in angina, myocardial infarction, atheroma and cardiac ischemia. Thromboxane $A_2$ ($TxA_2$) is the mediator most frequently involved in platelet aggregation and is the most powerful proaggregant agent which forms in the course of a metabolization path from arachidonic acid at the platelet level (F. Numano, Atherosclerose and antiplatelet therapy, Drugs of Today, 21, 41, 1985). In physiological disorders, the action of $TxA_2$ can be stopped during various stages of its formation and, in particular, by inhibiting either its synthesis or its action, by blocking the $TxA_2$ receptors causing aggregation.

The research on molecules antagonizing the $TxA_2$ receptors is a recent and promising approach for combating the damage caused by this. (Antithrombotic Agents, M. KUCHAR and V. REJMOLEC, Drug of the Future 11, 689, 1986; Comparison of the action of $TxA_2$ receptor antagonists, A. M. LEFER, Drugs of Today 21, 283, 1985).

The compounds of the present invention have the general formula I

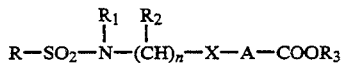

in which:
- R represents a straight-chain or branched lower alkyl radical containing from 1 to 9 C and, by way of non-limiting example: Me, Et, Pr, Bu, iBu . . . ;
  a phenyl radical which is unsubstituted or substituted by one or more groups: lower alkyl (1 to 4 C) or halogen or alkoxy, trifluoromethyl, nitro, amino, lower dialkylamino (1 to 4 C) and, by way of non-limiting example: Me, Et, i-Pr, F, Cl, Br, MeO, EtO, $NO_2$, $NH_2$, $NMe_2$, $CF_3$;
  a naphthyl radical which is unsubstituted or substituted as above; or a thiophenyl radical;
- $R_1$ represents a hydrogen or a straight-chain or branched $C_{1-4}$ lower alkyl, a benzyl and, by way of non-limiting example: Me, Et, i-Pr;
- $R_2$ represents a hydrogen, a straight-chain or branched lower alkyl group having 1 to 6 C and, by way of non-limiting example: Me, Et, i-Pr, i-Bu;
  a phenyl group which is unsubstituted or substituted by a chlorine or a methoxy;
  an arylalkyl group containing 7 to 9 carbon atoms;
- $R_3$ represents a hydrogen or a straight-chain or branched lower (1 to 6 C) alkyl and, by way of non-limiting example: Me, Et, i-Pr, i-Bu;
- X represents a divalent functional radical chosen from the following: $—CH_2—$; $—CH—OR_4$; $—C=O$; $—C=N—OR_4$;
  and

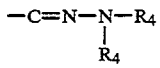

where $R_4 = H$ or Me.

A represents a benzo-carbocyclic or benzo-heterocyclic bivalent radical chosen from the following (a) to (j):

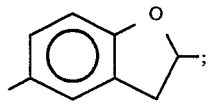 (a)

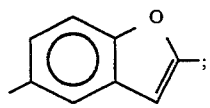 (b)

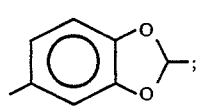 (c)

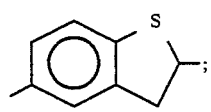 (d)

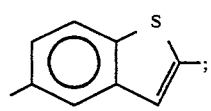 (e)

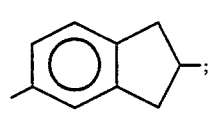 (f)

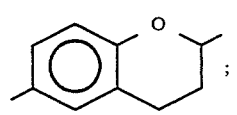 (g)

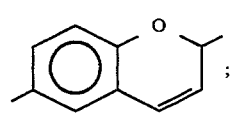 (h)

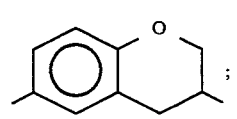 (i)

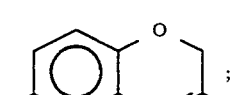 (j)

n = 1 to 4 inclusive.

The present invention also includes the therapeutically acceptable inorganic or organic salts of compounds of the general formula I in which $R_3 = H$ and, by way of non-limiting example, the sodium, calcium, zinc, 2-hydroxyethylammonium, bis(2-hydroxyethyl)ammonium and tris(2-hydroxyethyl)ammonium salts and also their hydrates where appropriate and the hydrates of the precursor acids.

When the compounds of general formula I contain at least one asymmetric carbon, the present invention also relates to the racemic mixtures and the various enantiomers or diasteroisomers or their mixtures.

The present invention also relates to the use of the compounds of general formula I as a medicament and to the pharmaceutical compositions containing this medicament. The pharmaceutical compositions according to the present invention can use one or more compounds of formula I, if appropriate in combination with one or more other active principles.

Finally, the processes for synthesis of the compounds of general formula I also form part of the present invention.

SYNTHESIS OF THE COMPOUNDS OF GENERAL STRUCTURE I

The base starting material for all of the syntheses is the ester of the acid in the 2- or 3-position of the indane derivative or benzo-heterocycle envisaged (compound II), where A has the same meaning as in I, with the exception of the radicals b, e, h, and j, and where $R_5$ has the same value as $R_3$ defined in I, with the exception of hydrogen.

In a first period, the compound II is subjected to a Friedel-Crafts reaction with the aid of a suitably substituted acid chloride of general formula III, where n and $R_2$ have the same meaning as in the formula I and where Y represents a halogen (bromine or chlorine) or an alkoxycarbonylamino of formula $R_8OCONR_1$ (where $R_8$ represents a straight-chain lower alkyl or a benzyl) to give the corresponding acyl derivative IV (method A).

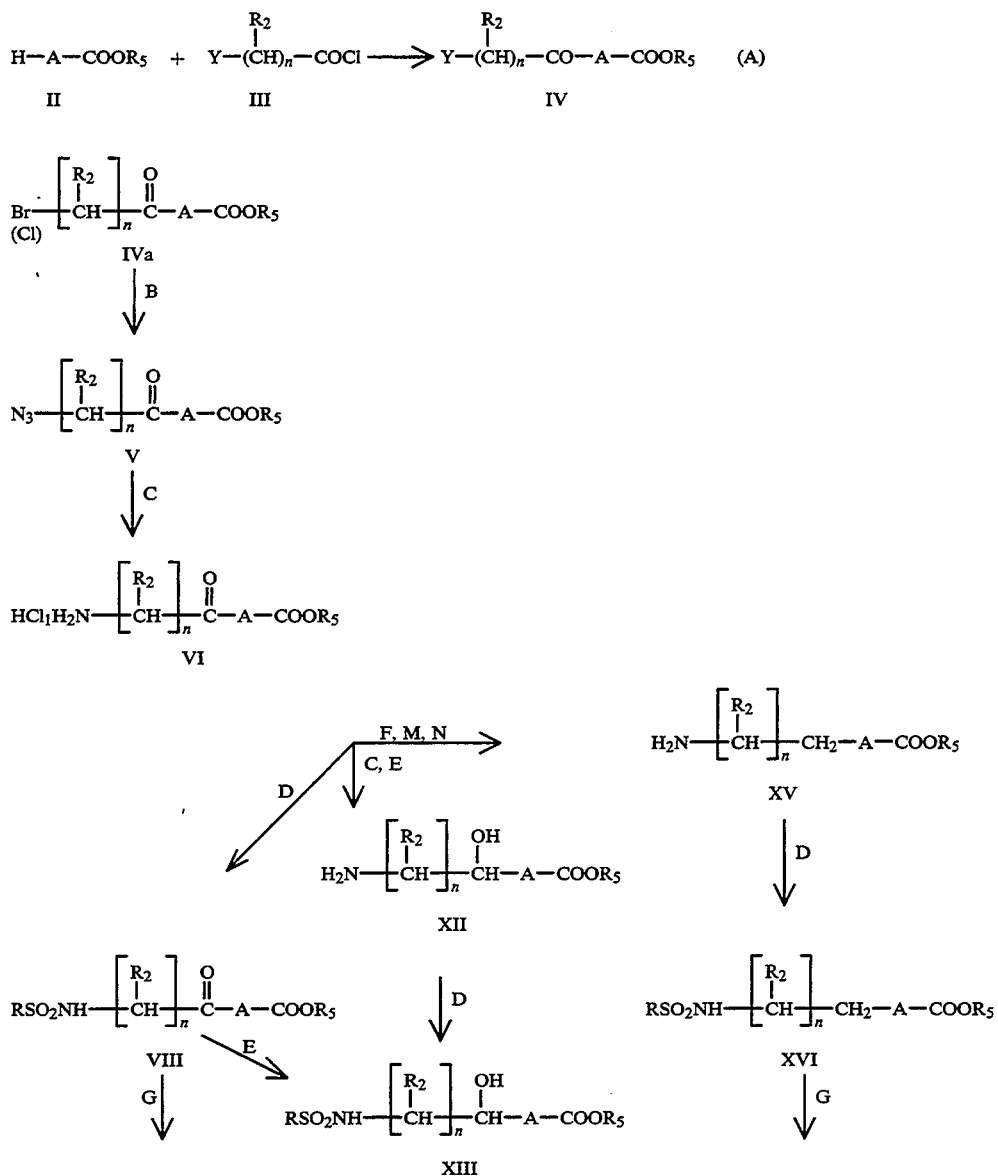

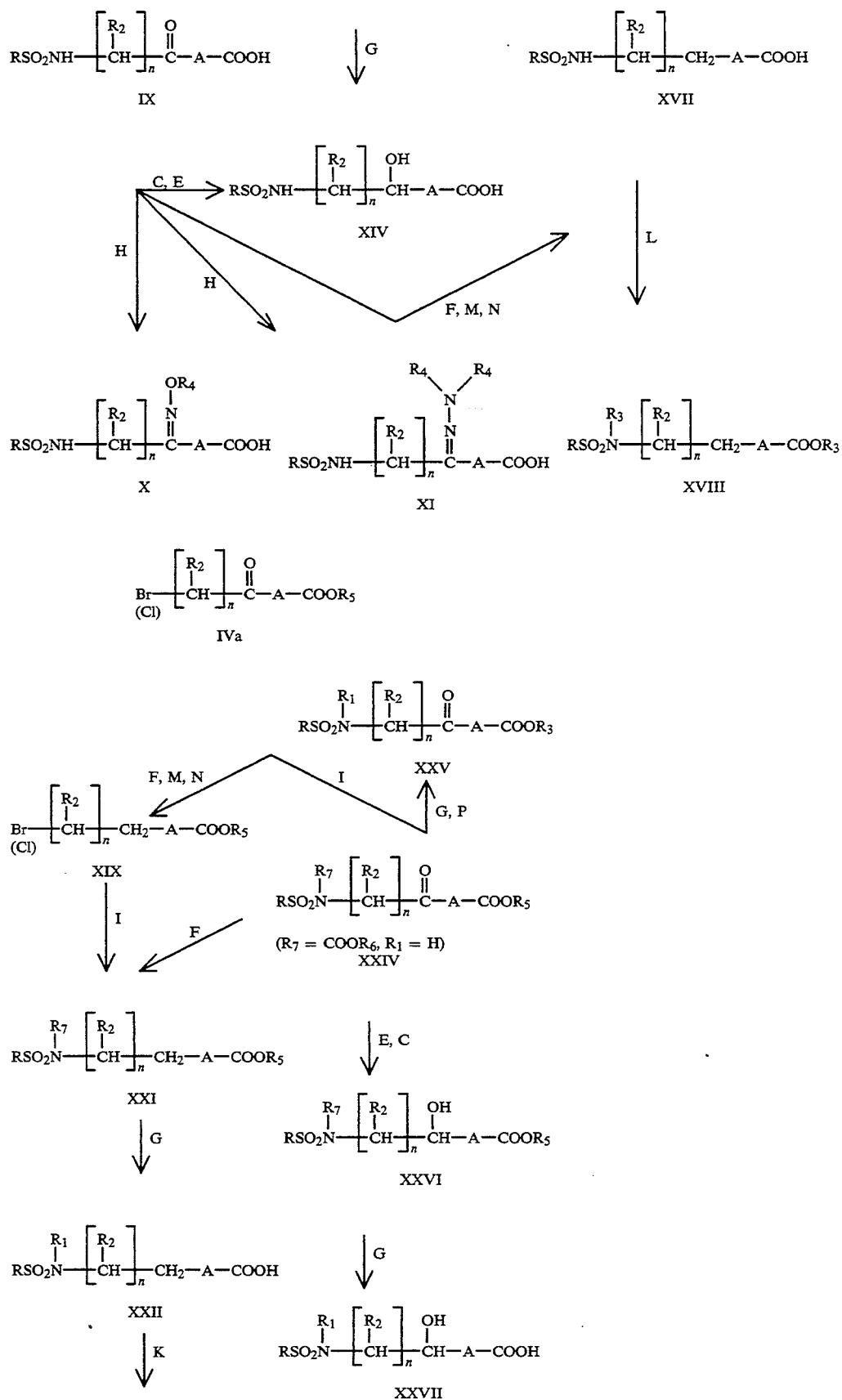

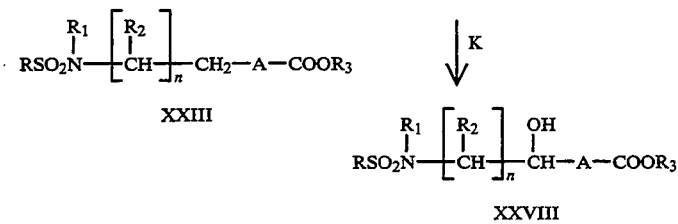

In a second period, the compound IV is reacted according to the synthesis scheme I in the case where Y is a halogen (chlorine or bromine) or according to the synthesis scheme II in the case where Y represents an alkoxycarbonylamino to give the compounds of general formula I, which are the subject of the present invention.

In these schemes the radicals have the same meaning as in I and the new groups are defined in the synthesis scheme.

1) Case where Y represents a halogen (bromine, chlorine) in IV (scheme 1)

The condensation reaction of IVa with sodium nitride in an aqueous-alcoholic mixture yields the compound V (method B), and the latter compound is reduced with hydrogen in the presence of a catalyst in an acid-alcoholic medium to give the esterified amino ketone in the form of a salt VI (hydrochloride for example) (method C). The condensation reaction of the above derivative VI with a suitably substituted sulphonyl halide of general formula VII $$R-SO_2-Z \qquad VII$$

where R has the same meaning as in I and Z represents a chlorine or a bromine or a fluorine, is effected using an organic base (pyridine for example) to give the ester VIII of I where $R_1=H$ (method D). This ester can be saponified in a dioxane or alcohol/sodium hydroxide mixture to give the sulphamido-keto-acid IX of general formula I where $R_1$ and $R_3=H$ (method G). This keto-acid IX reacts with unsubstituted or substituted hydroxyl-amines of formula $$R_4ONH_2$$

under hot conditions in pyridine to give the corresponding oximes X (method $H_1$). The condensation reaction with an unsubstituted or substituted hydrazine of formula:

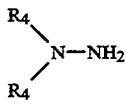

in an organic acid under hot conditions leads to the corresponding hydrazone XI (method $H_2$). If the hydrogenation of compound V is continued further, it can lead to the amino-alcohol XII via the intermediate VI (method C). This amino-alcohol can also be prepared from the ketone compound by reduction with a borohydride (Na or K) in an alcoholic medium (method E). It is preferable to use the same alcohol as that of the ester function since if it is different the transesterified compound XII is obtained. The hydroxysulphamido ester XIII can be obtained either from the ketone derivative IX by method E or by a condensation reaction of the sulphonyl halide of formula VII with the above amino compound XII (method D). Saponification of this compound carried out by method G gives the hydroxysulphamide acid XIV. The action of triethylsilane in a trifluoroacetic acid medium on the aminoketo ester VI enables the carbonyl selectively to be reduced to methylene to give the amino ester XV (method F). This compound also forms according to method C in a strong acid medium (method N). The condensation reaction of XV with the corresponding sulphonyl chloride (method D) gives the sulphamido ester XVI, which is saponified by the same method G to give the corresponding saturated acid compound XVII. The latter can also be obtained from the corresponding ketone derivative IX, either by reduction with triethylsilane (method F) or by catalytic hydrogenation in a strong acid medium (method M) or by reduction by the Clemmensen method in a nascent hydrogen medium (zinc/concentrated hydrochloric acid) in toluene (method N). The dialkylation of XVII in the presence of halides (bromide, iodide) $R_3I$ or of the corresponding sulphate $(R_3)_2SO_4$ leads, after formation of the disodium derivative, to the esterified and N-alkylated compound in which $R_1=R_3$ of formula XVIII (method L).

According to scheme I, the carbonyl in the intermediate IVa can be reduced to methylene to give the halogeno ester XIX, either with the aid of the $Et_3SiH/CF_3COOH$ system (method F) or by catalytic hydrogenation in a strong acid medium (method M) or by a Clemmensen reduction in a Zn/concentrated HCl medium in the presence of toluene under hot conditions (method N). This bromo ester XIX easily undergoes condensation under hot conditions in DMF with the sodium salt of secondary sulphonamides of general formula XX $$R-SO_2NH-R_7 \qquad XX$$

in which $R_7=R_1$ (except for H), or $COOR_6$, where $R_6$=straight-chain or branched alkyl or benzyl, to give the sulphonamide completely substituted on the nitrogen XXI (method I). Saponification by method G leads to the corresponding acid XXII. The latter can be esterified under hot conditions in an alcoholic medium ($R_3OH$) in the presence of a strong acid (concentrated $H_2SO_4$) (method K) to give the corresponding ester XXIII.

The starting intermediate IV can also be directly subjected to the condensation reaction with the sodium salt of the compound of general formula XX to give the corresponding sulphonamide (method I), of formula XXIV. The latter can be saponified under the operating conditions G to give the corresponding ketosulphonamido acid XXV. In the case where $R_7$ represents a tert.-butoxycarbonyl radical, the reaction is preceded by cleavage of the group in a hydrochloric medium in ethyl acetate (method P) to give the ester XXV where $R_1=H$, which is then saponified to the acid $R_3=H$ by method G. The ketone function of the compound XXIV can also be completely or partially reduced as for the compound IX. The partial reduction of XXIV yields the hydroxysulphamido ester XXVI (methods C and E); this derivative is then saponified to give the acid derivative XXVII (method G), which can be esterified to compound XXVIII in alcohol under hot conditions in a sulphuric medium (method K). The total reduction of the carbonyl of XXIV to $CH_2$ (compound XXI) is carried out by one of the three methods F, M and N described above. The sulphamido ester is easily saponified by process G to the corresponding acid XXII.

2) Case where Y represents an alkoxy or benzyloxycarbonyl in IV (synthesis scheme II)

The keto-ester carbamate of general formula IVb where $R_8$ represents a lower ($C_1$ to $C_8$) straight chain alkyl can also be partially reduced to the hydroxy derivative or totally reduced to $CH_2$. The partial reduction of IVb to compound XXIX is carried out in an alcoholic solvent in the presence of borohydride (method E). The removal of the protective group to give the aminohydroxy acid XXX by method G must be carried out in a more concentrated basic medium and under hot conditions. The aminohydroxy acid XXX, or its crude sodium salt, is then subjected to a condensation reaction with a sulphonyl halide of general formula VII in a basic aqueous medium, for example in sodium hydroxide at a pH of between 9 and 11, to give, after acidification, the acid XXVII.

3) The derivatives containing an unsaturated heterocycle —A— are prepared from saturated esters of general formula XXI or XXIV by substituent bromination with the aid of N-bromosuccinimide and simultaneous debromohydration under hot conditions in a chlorinated solvent such as $CCl_4$ for example, to give the corresponding ester XXXIII (method R), followed by saponification by method G to lead to the acid XXXIV in the furan series for example Synthesis scheme III

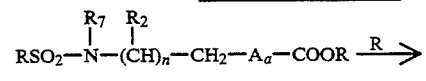

XXI ou XXIV

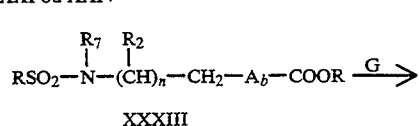

XXXIII

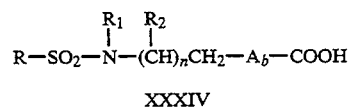

XXXIV

4) The organic or inorganic salts of compounds of general formula I where $R_3=H$ are prepared by a stoichiometric reaction between the compound I ($R_3=H$) and an organic or inorganic base (in the hydroxy or alcoholate form) in an alcoholic solvent or an alcohol/water mixture or in acetone. The salt is recovered by

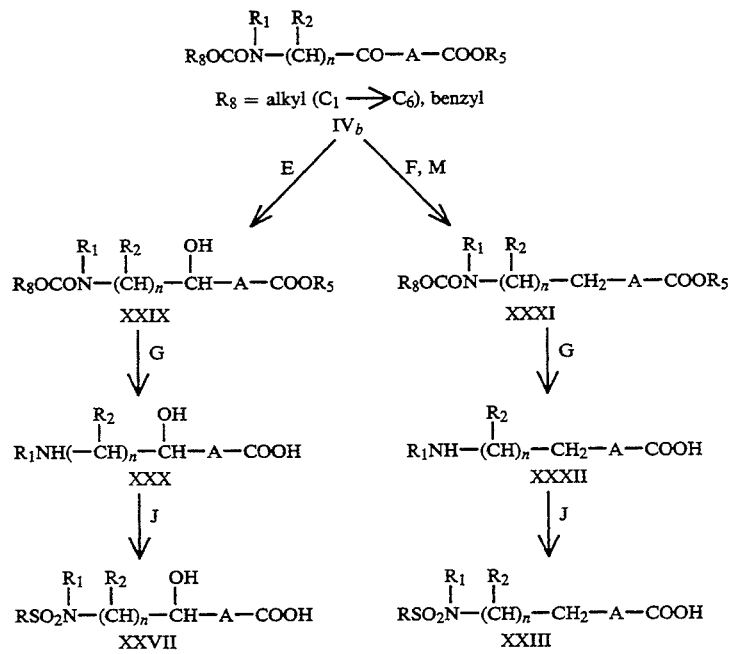

In a parallel manner, the reduction of the carbonyl in IVb to $CH_2$ can be carried out by methods F and M to give the compound XXXI, from which the protective groups are removed under the same conditions as for XXX to give the corresponding amino acid XXXII. This amino acid, or its sodium salt in the crude state, is subjected to a condensation reaction with the sulphonyl halide VII according to method K to yield the compound XXII.

filtration (if insoluble) or by evaporation of the solvent to dryness and recrystallization if necessary.

EXAMPLE 1

Preparation of 5-(parachlorobenzenesulphonamidoacetyl)-2,3-dihydro-2-benzofurancarboxylic acid (compound 1)

1a) Ethyl 5-bromoacetyl-2,3-dihydro-2-benzofurancarboxylate IV (Y=Br, $R_2$=H, A=a, $R_5$=Et, n=1) (1a) Method A)

A solution of 42.5 g (0.22 mole) of ethyl 2,3-dihydro-2-benzofurancarboxylate and 58.1 g (0.288 mole) of bromoacetyl bromide in 500 ml of methylene chloride is cooled to 0° C. and then treated in the course of 15 minutes with 73.3 g (0.55 mole) of anhydrous aluminum chloride. The mixture is stirred for a further 1 hour at 0° C. and then allowed to return slowly to 20° C. in the course of 3 hours. The mixture is hydrolysed at 0° C. with concentrated hydrochloric acid in the customary manner and then extracted with methylene chloride and the extract is washed with water and dilute sodium bicarbonate, dried and evaporated to dryness (80 g). The residue is recrystallized from 250 ml of boiling isopropyl alcohol, seeding with stirring. When cold, 56 g (yield=81%) of the intermediate of formula 1a re recovered

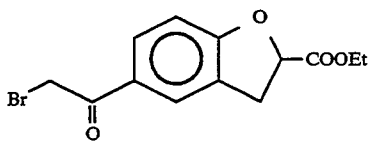

Compound 1a
empirical formula: $C_{13}H_{13}BrO_4$
molecular weight: 313.152
broken white crystals
melting point: 70° C.
IR (KBr): $\checkmark$CO 1675, $\checkmark$COOEt 1750 cm$^{-1}$.
NMR (CDCl$_3$) δ: 1.32, t, 3H, CH$_3$; 3.40, q, 1H, ArCH$_2$C(O)COOEt; 3,62, q, 1H, ArCH$_2$C(O)COOEt; 4.28, q, 2H, COOCH$_2$Me; 4.38, s, 2H, BrCH$_2$CO; 5.29, q, 1H, OCHCOOEt; 6.94, d, 1H, Ar ortho OCH$_2$; 7.84 to 7.88; m, 2H, Ar ortho CO.

1b) Ethyl 5-azidoacetyl-2,3-dihydro-2-benzofurancarboxylate V ($R_2$=H, n=1, A=a, $R_5$=Et) (1b) (method B)

A mixture of 10 g (32 mmoles) of ethyl 5-bromoacetyl-2,3-dihydro-2-benzofurancarboxylate (1a) in 130 ml of ethanol is cooled in an ice bath and then treated with a solution of 2.3 g (35 mmoles) of sodium nitride in 6 ml of water, added dropwise in the course of 10 min. The ice bath is removed and the solution is then stirred for 5 h at 25° C.

The expected derivative precipitates. After leaving in the refrigerator for 16 h, the crystals of the compound of formula 1b are recovered in the customary way

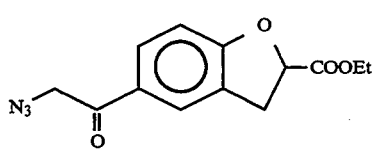

Compound 1b
empirical formula: $C_{13}H_{13}N_3O_4$
molecular weight: 275.264
white crystals
melting point: 85° C.
IR (KBr): $\checkmark$CO 1683, $\checkmark$COOEt 1738, $\checkmark$CN$_3$ 2125 cm$^{-1}$.
NMR (CDCl$_3$) δ: 4.49, s, 2H, N$_3$CH$_2$CO.

1c) Ethyl 5-aminoacetyl-2,3-dihydro-2-benzofurancarboxylate hydrochloride VI ($R_2$=H, n=1, A=a, $R_5$=Et) (1c) (method C).

A solution of 9.2 g (33.4 mmoles) of ethyl 5-azidoacetyl-2,3-dihydro-2-benzofurancarboxylate in 500 ml of methanol and 30 ml of N hydrochloric acid is hydrogenated in the customary manner in the presence of 1.5 g of 10% palladium-on-charcoal under a stream of hydrogen for 2 h 30. After purging with nitrogen, the catalyst is removed by filtration, the filtrate is evaporated to dryness, the residue is taken up in 100 ml of isopropyl alcohol and the mixture is stirred overnight at 25° C. The crystals consist of the compound of formula 1c and are recovered in the customary way (weight=6 g-yield=63%).

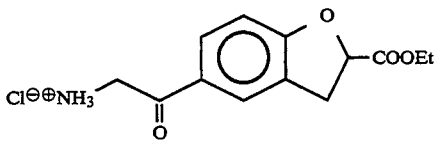

Compound 1c
empirical formula: $C_{13}H_{16}ClNO_4$
molecular weight: 285.727
white crystals
melting point: 152° C.
IR (KBr): $\checkmark$NH 3000, $\checkmark$COOEt 1740, $\checkmark$CO 1680 cm$^{-1}$.
NMR (CDCl$_3$) δ: 4.5 to 4.7, m, 2H, NCH$_2$CO. 1d) Ethyl 5-(parachlorobenzenesulphonamidoacetyl)-2,3-dihydro-2-benzofurancarboxylate VIII (R=p-ClC$_6$H$_4$—, $R_2$=H, n=1, A=a, $R_5$=Et; (and for I $R_1$=H and X=CO) (1d) (method D).

A suspension of 5.8 g (20.2 mmoles) of ethyl 5-aminoacetyl-2,3-dihydro-2-benzofurancarboxylate hydrochloride (1c) in 65 ml of pyridine cooled to −5° C. is treated with 5.5 g (26.1 mmoles) of parachlorobenzenesulphonyl chloride. The mixture is kept at this temperature for ¼ hour and stirring is then continued for a further 2 hours after returning to 20°. The reaction mixture is hydrolysd with 100 ml of water and then extracted with ethyl acetate. The organic phase is washed twice with 100 ml of water, the pH of which has been adjusted to 5.5 by the addition of concentrated HCl, and is then washed with saline water, dried over sodium sulphate and evaporated. The residue yields two amounts of crystals of formula 1d by dissolving in ethyl acetate and precipitating from ether or isopropyl ether (weight=6.3 g—yield =73%)

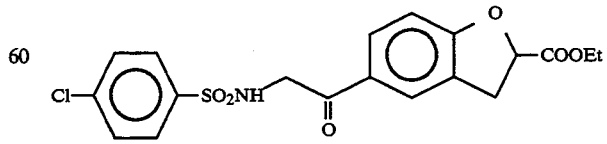

Compound 1d
empirical formula: $C_{19}H_{18}ClNO_6S$
molecular weight: 423.871
broken white crystals melting point: 153° C.

IR (KBr): √SO₂N 1160–1350, √CO 1688, √COOEt 1738, √NH 3300 cm⁻¹.

NMR (CDCl₃) δ: 4.39, d, 2H, NCH₂CO; 5.8, t, 1H, NH; 7.42 to 7.48, dd, 2H, Ar ortho of Cl; 7.78 to 7.84, dd, 2H, Ar ortho of SO₂ 1e) Saponification (method G), synthesis of 5-parachlorobenzenesulphonamidoacetyl-2,3-dihydro-2-benzofurancarboxylic acid IX (R=pCl C₆H₄, R₂=H, A=a; (I R₁=H, R₃=H, X=CO) (1)

At 25° C. a solution of 3.8 g (9 mmoles) of ethyl 5-parachlorobenzenesulphonamidoacetyl-2,3-dihydro-2-benzofurancarboxylate (1d) in 40 ml of methanol is brought to pH 11.8 by adding 10 ml of N sodium hydroxide solution. The pH is held at 11.5 by dropwise addition of 6 ml of N sodium hydroxide solution. Stirring is continued for 1 h 30 and the mixture is then cooled with ice and acidified to pH 3.3 by addition of N hydrochloric acid. After stirring for 20 min at 0° C., the crystals of the expected derivative are collected, rinsed with ice-water and dried (2.7 g). By recrystallization from isopropyl alcohol, 2.05 g (yield=58%) of crystals of compound 1 are recovered, of formula

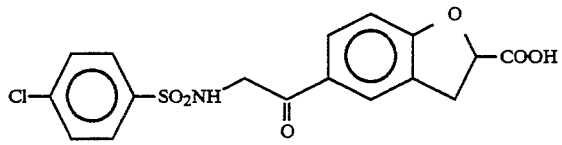

Compound 1
empirical formula: C₁₇H₁₄ClNO₆S
molecular weight: 395.817
broken white crystals
melting point: 124° C.
IR (KBr): √SO₂N 1170–1360, √CO 1695, √COOH 1730, √NH 3300 cm⁻¹.
NMR (CDCl₃) δ: 5.31, q, 1H, OCHCOO.
TLC: silica gel 60 Merck F 254
eluant: chloroform/methanol/acetic acid: 80/18/02
Rf=0.48
soluble in DMSO to give a 10% solution.

EXAMPLE 2

Preparation of 5-(2-parachlorobenzenesulphonamidoethyl)-2,3-dihydro-2-benzofurancarboxylic acid (compound 2)

a) Sodium salt of N-ethoxycarbonylparachlorobenzenesulphonamide XX (R₇=EtOCO, R=p-ClC₆H₄; Na salt) (2a)

A mixture formed from 85 g (0.443 mole) of parachlorobenzenesulphonamide and 157.2 g (1.13 mole) of K₂CO₃/KI 98/02 in 500 ml of acetone is treated at 25° C. with 62.6 g (0.576 mole) of ethyl chloroformate, added dropwise in the course of 30 min, with mechanical stirring. The reaction is slightly exothermic and, after the temperature has stabilized at 40° C., the mixture is brought progressively to reflux for 2 hours. After cooling, the mixture is poured into 500 ml of crushed ice and the sulphonamide is extracted with ether. The residue obtained after washing, drying and evaporating to dryness is dissolved in 80 ml of hot isopropyl ether and is then precipitated by adding cyclohexane to obtain 100 g (yield =86%) of white derivative of formula

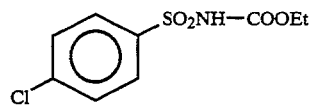

empirical formula: C₉H₁₀ClNO₄S
molecular weight: 263.70
broken white crystals
melting point: 80° C.

Twenty grams (75.8 mmoles) of the above sulphonamide are added at 25° C. to a methanolic solution of sodium methylate (prepared from 1.75 g (75.8 mmoles) of sodium) while cooling in a bath of cold water and the mixture is then stirred for 2 h 30 at 25° C. The mixture is evaporated to dryness and the residue is then triturated and stirred overnight in 250 ml of ether. The insoluble matter formed by compound 2a is recovered by filtration (weight=14 g-yield=65%).

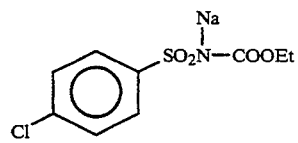

Compound 2a
empirical formula: C₉H₉ClNNaO₄S
molecular weight: 285.68
white crystals
melting point: 220° C.

b) Ethyl 5-(N-ethoxycarbonylparachlorobenzenesulphonamidoacetyl)-2,3-dihydro-2-benzofurancarboxylate XXIV (R=p-ClC₆H₄⁻, R₇=EtOCO, R₂=H, n=1, A=a, R₅=Et) (2b) (method I)

A mixture of 12.8 g (44.8 mmoles) of the above sodium salt of N-ethoxycarbonylparachlorobenzenesulphonamide (2a) in 200 ml of DMF cooled to 4° C. in an ice bath is treated rapidly with 12.79 g (40.7 mmoles) of ethyl 5-bromoacetyl-2,3-dihydrobenzofurancarboxylate prepared as in Example 1a. Stirring is then continued overnight at 25° C. and then for 30 min in an oil bath at 50° C. After the temperature has returned to 25° C., the mixture is poured onto 400 ml of crushed ice and the expected derivative is extracted with ether and recovered in the customary manner. 22.4 g (yield=100%) of product of formula 2b are obtained. The product can be used in the crude form or purified from isopropyl alcohol.

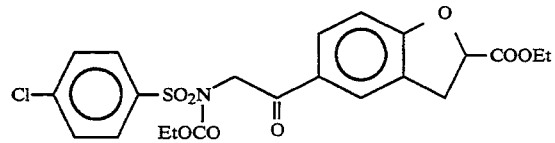

Compound 2b
empirical formula: C₂₂H₂₂ClNO₈S
molecular weight: 495.934
amorphous whitish powder
melting point: 98° C.
IR (KBr): √SO₂N 1170–1350, √CO 1700, √COOEt and NCOOEt 1755 cm⁻¹.
NMR (CDCl₃) δ: 1.12, t, 2H, NCOOCH₂CH₃; 4.12, q, 2H, NCOOCH₂CH₃; 5.27, s, 2H, COCH₂N; 7.51, d, 2H, Ar ortho of Cl; 8.03, d, 2H. Ar ortho of SO₂.

2c) 5-(2-(N-ethoxycarbonylparachlorobenzenesulphonamido)ethyl)-2,3-dihydro-2-benzofurancarboxylate XXI (R=p-ClC$_6$H$_4$—, R$_7$=EtOCO—, R$_2$=H, A=a, R$_5$=Et) (method F)

A solution of 22.4 g (40.7 mmoles) of the above crude ethyl 5-(N-ethoxycarbonylparachlorobenzenesulphonamidoacetyl)-2,3-dihdyrobenzofurancarboxylate (2b) in 80 ml of CF$_3$COOH is treated at 25° C. with 19.5 ml (14.19 g or 122 mmoles) of triethylsilane and the mixture is stirred for 24 h. The solution formed is evaporated to dryness under vacuum and the residue is then taken up in toluene and the solution is evaporated to dryness to give the compound 2c, which can be used in the crude form (yield=100%) or purified on a normal silica column eluting with a mixture of 60% of cyclohexane, 30% of methylene chloride and 10% of ethyl acetate to give the compound 2c in a yield of 70%, this compound having the formula

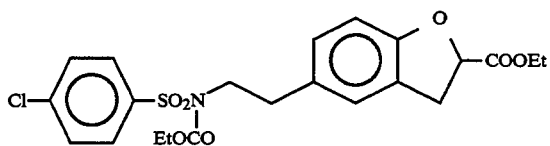

Compound 2c
empirical formula: C$_{22}$H$_{24}$ClNO$_7$S
molecular weight: 481.951
colourless oil
IR (film): $\sqrt{}$SO$_2$N 1170–1350, $\sqrt{}$COOEt and NCOOEt 1755 cm$^{-1}$. NMR (CDCl$_3$) δ: 2.96, t, 2H, ArCH$_2$CH$_2$N; 4, t, 2H, ArCH$_2$CH$_2$N; 7 to 7.06, m, 2H, Ar ortho to CH$_2$.

2d) 5-(2-Parachlorobenzenesulphonamidoethyl)-2,3-dihydro-2-benzofurancarboxylic acid XXII (R=p-ClC$_6$H$_4$, R$_1$=R$_2$=H, n=1, A=a and for I, X=CH$_2$, R$_5$=H) (compound 2) (method G)

The above crude ethyl 5-(2-(N-ethoxycarbonylparachlorobenzenesulphonamido)ethyl)-2,3-dihydro-2-benzofurancarboxylate (2c) (40.7 mmoles) is taken up in 80 ml of dioxane and the solution is then treated with 80 ml of 5N sodium hydroxide solution and heated with stirring at 50° C. for 15 min. The mixture is poured into 500 ml of ice and extracted with ether. The aqueous phase is acidified to pH 5. The expected acid is extracted with ethyl acetate in the customary manner and the residue is triturated in ether and then stirred for 1 h at 25° C. 11.45 g (yield=74%) of pulverulent white crystals of compound 2 are recovered, this compound having the formula

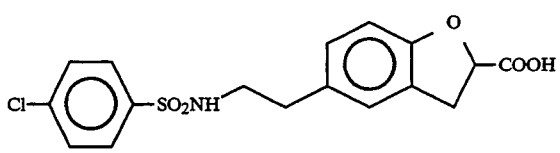

Compound 2
empirical formula: C$_{17}$H$_{16}$ClNO$_5$S
molecular weight: 381.834
pulverulent white crystals
melting point: 153° C.
IR (KBr): $\sqrt{}$SO$_2$N 1160–320, $\sqrt{}$COOH 1700, $\sqrt{}$NH 3240 cm$^{-1}$.
NMR (CDCl$_3$) δ: identical to that of compound 4.
TLC: silica gel 60 Merck F 254 eluant: chloroform/methanol/acetic acid: 80/18/02 Rf=0.45
soluble in DMSO to give a 10% solution.

EXAMPLE 3

Preparation of 5-(2-parachlorobenzenesulphonamido-1-hydroxyethyl)-2,3-dihydro-2-benzofurancarboxylic acid (compound 3) (synthesis scheme II)

a) Ethyl 5-ethoxycarbonylaminoacetyl-2,3-dihydro-2-benzofurancarboxylate IV (Y=EtOCONH—, R$_2$=H, n=1, A=a, R$_5$=Et) (3a)

Using the operating method A described in Example 1 for compound 1a but replacing bromoacetyl bromide by ethoxycarbonylaminoacetyl chloride prepared in situ from 36.1 g (0.245 mole) of the corresponding acid and subjecting it to a condensation reaction with 24.8 g (0.129 mole) of ethyl 2,3-dihydrobenzofurancarboxylate in the presence of 86 g (0.645 mole) of aluminium chloride, 11.4 g (yield=28%) of compound 3a are obtained after purification on a silica column (C$_6$H$_{12}$-AcOEt-CH$_2$Cl$_2$: 60/20/20) and recrystallization from isopropyl ether, compound 3a having the formula

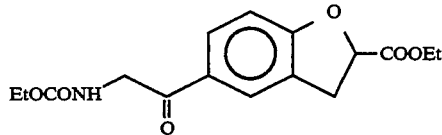

Compound 3a
empirical formula: C$_{16}$H$_{19}$NO$_5$
molecular weight: 321.329
broken white crystals
melting point: 82° C.
IR (KBr): $\sqrt{}$NCOOEt 1670, $\sqrt{}$CO 1700, $\sqrt{}$COOEt 1730 cm$^{-1}$. NMR (CDCl$_3$) δ: 1.24 to 1.35, m, 6H, 2 CH$_3$; 3.34 to 3.68, m, 2H, OCHCH$_2$; 4.10 to 4.33, m, 4H, 2 CH$_2$; 4.62, d, 2H, NCH$_2$CO; 5.29, q, 1H, OCHCH$_2$; 5.7, t, 1H, NH; 6.95, d, 1H, Ar ortho O; 7.84.m, 2H, Ar ortho CO.

3b) Ethyl 5-(2-ethoxycarbonylamino-1-hydroxyethyl)-2-benzofurancarboxylate XXIX (R$_8$=Et, R$_1$=R$_2$=H, n=1, A=a, R$_5$=Et) (3b) (method E)

A mixture of 3.2 g (10 mmoles) of the above ethyl 5-(2-ethoxycarbonylaminoacetyl)-2,3-dihydro-2-benzofurancarboxylate 3a in 30 ml of ethanol is treated at 25° C. with 0.27 g (5 mmoles) of potassium borohydride. After stirring for 2 h 30, 0.11 g (2 mmoles) of supplementary KBH$_4$ are added and the mixture is kept at 25° C. for a further one hour. The reaction mixture is poured into saturated saline water and extracted with ether and the extract is then washed with water and with saline water and finally dried over sulphate and evaporated to dryness. The residue is purified on a silica column eluting successively with a 90/10 hexane/ethyl acetate mixture and then a 60/20/20 cyclohexane/methylene chloride/ethyl acetate mixture. The fractions containing the expected derivative are evaporated to dryness and the solid obtained is then taken up in isopropyl ether. The pulverulent crystals of the compound of formula 3b are recovered in the customary manner (weight=1.7 g-yield=53%)

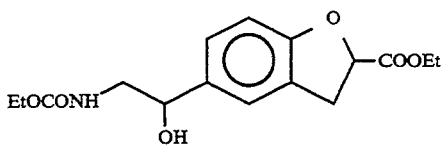

Compound 3b
empirical formula: $C_{16}H_{21}NO_6$
molecular weight: 323.345
broken white pulverulent crystals
melting point: 95° C.
IR (KBr): $\sqrt{}$NCOOEt 1680, $\sqrt{}$COOEt 1730-1750, $\sqrt{}$NH 3300, $\sqrt{}$OH 3370 cm$^{-1}$.
NMR (CDCl$_3$) δ: 3.15 to 3.60, m, 5H, ArC$\underline{H}_2$CHOAr and NC$\underline{H}_2$CHOH; 4.67 to 4.75, m, 1H, C$\underline{HOH}$; 6.83, d, 1H, Ar ortho of $\overline{OCH_2}$; 7.10, d and 7.18 s, $\overline{2H}$, Ar ortho CHOH.

3c) 5-(2-Amino-1-hydroxyethyl)-2,3-dihydro-2-benzofurancarboxylic acid XXX ($R_1=R_2=H$, n=1, A=a) (3c) (method G)

Using method G described in Example 2d, starting from 3 g (9.3 mmoles) of ethyl 5-(2-ethoxycarbonyl-1-hydroxyethyl)-2,3-dihydro-2-benzofurancarboxylate and after heating to reflux for 1 h 30, a solution of the sodium salt of acid XXX of formula 3c is obtained, which is not isolated

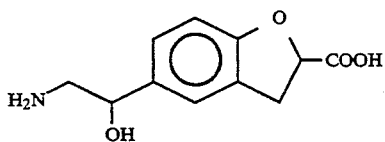

Compound 3c 3d) 5-(2-Parachlorobenzenesulphonamido-1-hydroxyethyl)-2,3-dihydro-2-benzofurancarboxylic acid XXVII (R=p-ClC$_6$H$_4$—, $R_1=R_2=H$, A=a and for I $R_5=H$ and X—CHOH) (compound 3) (method J)

The crude basic solution obtained in the above example 3c is diluted with crushed ice and brought to pH 11 by adding concentrated HCl and 3 g (14.2 mmoles) of parachlorobenzenesulphonyl chloride are then added. The mixture is then stirred for 4 h at 25° C., treated again with a further 0.5 g ($\approx$2.4 mmoles) of the above chloride and stirred for a further 2 h. The pH is brought to 12 by adding sodium hydroxide solution and the mixture is then extracted with ether. The basic aqueous phase is acidified (HCl) to pH 7 and extracted with ethyl acetate, then acidified to pH 2 and extracted with ethyl acetate in the customary manner. The residue (2 g) obtained after evaporating off the solvent is purified on a silica (20 g) column, eluting with a 99/01 AcOEt/AcOH mixture. The fractions containing the expected derivative are combined and evaporated to dryness.

The residue is triturated in isopropyl ether and the insoluble matter consisting of compound 3 is recovered in the customary manner (weight=1.6 g-yield=42%)

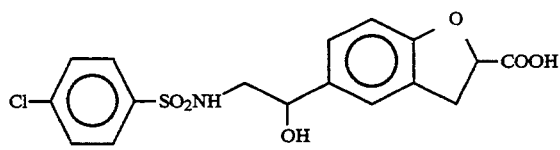

Compound 3
empirical formula: $C_{17}H_{16}ClNO_6S$
molecular weight: 397.83
pulverulent white crystals
melting point: 77° C. slow
IR (KBr): $\sqrt{}$SO$_2$NH 1150-1320, $\sqrt{}$COOH 1720, $\sqrt{}$NH 3400 cm$^{-1}$.
NMR (CDCl$_3$) δ: 2.7 to 3, m, 2H, NC$\underline{H}_2$CHOH; 4.46 to 4.52, q, 1H, C$\underline{H}$OH; 6.49 to 6.55, q, 1$\overline{H}$, N$\underline{H}$; 7.30, d, 2H, Ar ortho Cl; 7.60, d, 2H, Ar ortho SO$_2$.
TLC: silica gel 60 Merck F 254
eluant: chloroform/methanol/acetic acid: 80/18/02
Rf=0.35
soluble in DMSO to give a 10% solution.

EXAMPLE 4

Preparation of 5-(2-parachlorobenzenesulphonamidoethyl)-2,3-dihydro-2-benzofurancarboxylic acid monohydrate (compound 4) XXXIII (R=p-ClC$_6$H$_4$, $R_1=R_2=H$, n=1, A=a and for I X=CH$_2$, $R_3=H$, hydrate) (synthesis scheme II)

a) Ethyl 5-(2-ethoxycarbonylaminoethyl)-2,3-dihydro-2-benzofurancarboxylate XXXI ($R_6=Et$, $R_1=R_2=H$, n=1, A=a, $R_5=Et$) (method F).

Using the method described in Example 2c and starting from ethyl 5-ethoxycarbonylaminoacetyl-2,3-dihydro-2-benzofurancarboxylate (compound 3a), the derivative of formula 4a is obtained in a yield of 84%

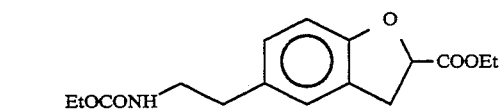

Compound 4a
empirical formula: $C_{16}H_{21}NO_5$
molecular weight: 307.346
white crystals
melting point: 63° C.
IR (KBr) $\sqrt{}$NCOOEt 1690, $\sqrt{}$COOEt 1735, $\sqrt{}$NH 3300 cm$^{-1}$.
NMR (CDCl$_3$) δ: 2.73, t, 2H, ArC$\underline{H}_2$CH$_2$N; 3.37, t, 2H, ArCH$_2$C$\underline{H}_2$N; 6.96, d, 1H, and 7.00, s, 1H, Ar ortho of CH$_2$CH$_2$.

4b) 5-(2-Parachlorobenzenesulphonamidoethyl)-2,3-dihydro-2-benzofurancarboxylic acid monohydrate XXXIII (methods G and J consecutively).

Starting from ethyl 5-(2-ethoxycarbonylaminoethyl)-2,3-dihydro-2-benzofurancarboxylate and adapting the operating method of Example 3c according to method G, the sodium salt of the acid:

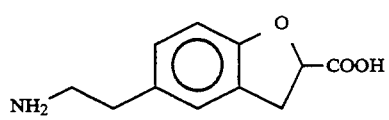

is obtained as an intermediate, which is not isolated but is directly subjected to a condensation reaction with parachlorobenzenesulphonyl chloride according to method J described in Example 3d to give, in a yield of 63%, compound 4 of formula

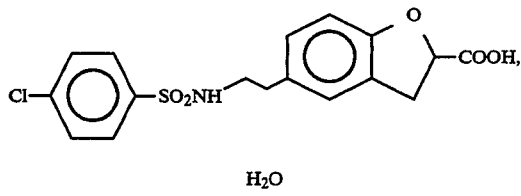

H₂O

Compound 4
  empirical formula: C₁₇H₁₈ClNO₆S
  molecular weight: 399.849
  white crystals
  melting point: 124° C.
  IR (KBr): √SO₂N 1160–1320, √COOH 1700, √NH 3240 cm⁻¹.
  NMR (CDCl₃) δ: 2.4, t, 2H, ArCH₂CH₂—N; 2.75, q, 2H, ArCH₂CH₂N; 2.95 to 3.3, m, 2H, ArCH₂CHO; 4.86, q, 1H, ArCH₂CHO; 6.45, d, 1H, Ar ortho O; 6.6, d, 1H, Ar ortho CH₂CH₂; 6.65, s, 1H, Ar ortho CH₂CH₂ and CH₂CHO; 6.91, t, 1H, NH; 7.17, d, 2H, Ar ortho Cl; 7.47, d, 2H, Ar ortho SO₂.
  TLC: silica gel 60 Merck F 254
  eluant: chloroform/methanol/acetic acid: 90/09/01
  Rf=0.16
  soluble in DMSO to give a 10% solution.

EXAMPLE 5

Preparation of 5-(α-methylparachlorobenzenesulphonamidoacetyl)-2,3-dihydro-2-benzofurancarboxylic acid IX (R=p-ClC₆H₄, R₂=Me, n=1, A=a and for I X=CO and R₅=H) (compound 5) (synthesis scheme I)

a) Ethyl 5-α-bromopropionyl-2,3-dihydro-2-benzofurancarboxylate IV (Y=Br, R₂=Me, n=1, A=a, R₅=Et). Adapting the operating method A described in Example 1a to α-bromopropionyl bromide, compound 5a is obtained in a yield of 72%, this compound having the formula

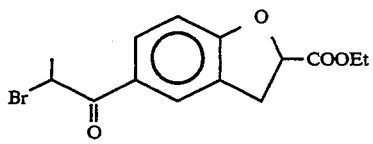

Compound 5a
  empirical formula: C₁₄H₁₅BrO₄
  molecular weight: 327.179
  white crystals
  melting point: 97° C.
  IR (KBr): √CO 1680, √COOEt 1760 cm⁻¹.
  NMR (CDCl₃) δ: 1.32, t, 3H, CH₂CH₃; 1.88, d, 3H, CHCH₃; 3.35 to 3.68, m, 2H, OCHCH₂; 4.28, q, 2H, CH₂CH₃; 5.19 to 5.34, m, 2H, CHCH₃ and OCHCH₂; 6.95, d, 1H, Ar ortho O; 7.89 to 7.92, m, 2H, Ar ortho CO.

b) Ethyl 5-(α-azidopropionyl)-2,3-dihydro-2-benzofurancarboxylate V (R₂=Me, n=1, A=a, R₅=Et). Using the operating method used to prepare compound 1b, starting from ethyl 5-(α-bromopropionyl)-2,3-dihydro-2-benzofurancarboxylate, compound 5b is obtained in a yield of 100%, this compound having the formula

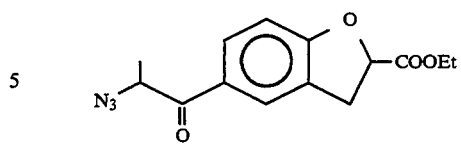

Compound 5b
  empirical formula: C₁₄H₁₅N₃O₄
  molecular weight: 289.291
  colourless oil.

c) Ethyl 5-(α-aminopropionyl)-2,3-dihydrobenzofurancarboxylate hydrochloride VI (R₂=Me, n=1, A=a, R₅=Et) (5c)
  Adaptation of operating method C (cf. Example 1c) to ethyl 5-(α-azidopropionyl)-2,3-dihydro-2-benzofurancarboxylate (5b) enables compound 5c to be prepared in a yield of 61.4%, this compound having the formula

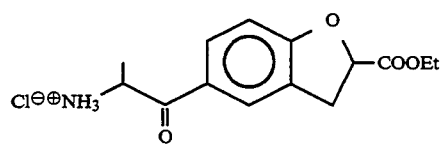

Compound 5c
  empirical formula: C₁₄H₁₈ClNO₄
  molecular weight: 299.754
  white crystals.

d) Ethyl 5-(α-methylparachlorobenzenesulphonamidoacetyl)-2,3-dihydro-2-benzofurancarboxylate VIII (R=p-ClC₆H₄—, R₂=Me, n=1, A=a, R₅=Et) (5d).
  Adapting operating method D (cf. Example 1d) to ethyl 5-(α-aminopropionyl)-2,3-dihydro-2-benzofurancarboxylate hydrochloride, compound 5d is obtained in a yield of 45%, this compound having the formula

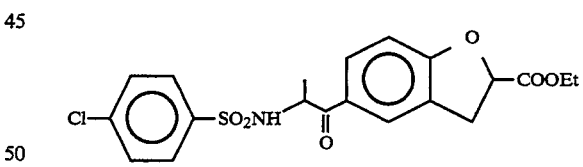

Compound 5d
  empirical formula: C₂₀H₂₀ClNO₆S
  molecular weight: 437.898
  broken white crystals
  melting point: 137° C.
  IR (KBr): √SO₂N 1170–1355, √CO 1670, √COOEt 1755, √NH 3280 cm⁻¹.

5e) 5-(α-Methylparachlorobenzenesulphonamidoacetyl)-2,3-dihydro-2-benzofurancarboxylic acid (compound 5).

Using operating method G (cf. Example 1e) to saponify ethyl 5-(α-methylparachlorobenzenesulphonamidoacetyl)-2,3-dihydro-2-benzofurancarboxylate, compound 5 is obtained in a yield of 63%, this compound having the formula

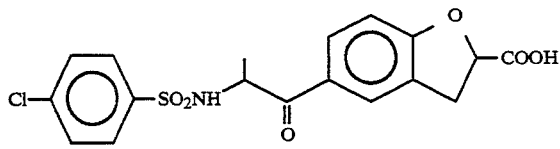

Compound 5
 empirical formula: $C_{18}H_{16}ClNO_6S$
 molecular weight: 409.844
 white crystals
 melting point: 134°–136° C.
 IR (KBr): $\sqrt{}SO_2N$ 1175–1355, $\sqrt{}CO$ 1670, $\sqrt{}COOH$ 1730, $\sqrt{}NH$ 3290 cm$^{-1}$.
 NMR (CDCl$_3$) δ: 1.37, d, 3H, CH$_3$; 3.33 to 3.70, m, 2H, CH$_2$CHO; 4.84, m, 1H, CHCH$_3$; 5.27, q, 1H, CH$_2$CHO; 6.1, d, 1H, NH; 6.9, d, 1H, Ar ortho O; 7.33, d, 2H, Ar ortho Cl; 7.62 to 7.8, m, 4H, Ar ortho SO$_2$ and Ar ortho CO.
 TLC: silica gel 60 Merck F 254 eluant: chloroform/methanol/acetic acid: 80/18/02 Rf=0.49
 soluble in DMSO to give a 10% solution.

EXAMPLE 6

5-(2-Parachlorobenzenesulphonamido-1-hydroxypropyl)-2,3-dihydro-2-benzofurancarboxylic acid XIV (R=p-Cl—C$_6$H$_4$—, R$_2$=Me, n=1, A=a, and for I R$_1$=R$_3$=H, and X=CHOH) (scheme I) (compound 6)

a) Ethyl 5-(2-amino-1-hydroxypropyl)-2,3-dihydro-2-benzofurancarboxylate XII (R$_2$=Me, n=1, A=a, R$_5$=Et) (6a). Starting from 21 mmoles of ethyl 5-(α-azidopropionyl)-2,3-dihydro-2-benzofurancarboxylate already described in Example 5b and using method C but hydrogenating for a much longer period, 2.5 g (yield=45%) of compound 6a are obtained after purification on a silica column and eluting with a 90/09/01 chloroform/methanol/ammonia mixture, compound 6a having the formula

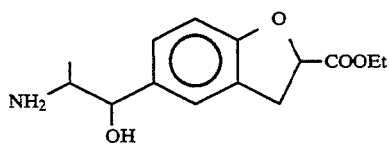

Compound 6a
 empirical formula: $C_{14}H_{19}NO_4$
 molecular weight: 265.31
 broken white crystals
 melting point: 115° C.
 IR (KBr): $\sqrt{}COOEt$ 1730, $\sqrt{}NH$ and OH 3280–3340 cm$^{-1}$.
 NMR (CDCl$_3$) δ: 0.86, d, 3H, CH$_3$CH; 1.19, t, 3H, CH$_3$CH$_2$; 2.95, m, 1H, CHCH$_3$; 3.15 to 3.50, m, 2H, ArCH$_2$CHO; 3.68, s, 1H, OH; 4.13, q, 2H, CH$_3$CH$_2$; 4.26, d, 1H, CHOH; 5.03 to 5.15, m, 1H, ArCH$_2$CHO; 6.70, d, 1H, Ar ortho O; 6.95, d, 1H and 7.07, s, 1H, Ar ortho CHOH.

b) Ethyl 5-(2-parachlorobenzenesulphonamido-1-hydroxypropyl)-2,3-dihydro-2-benzofurancarboxylate XIII (R=p-Cl—C$_6$H$_4$, R$_2$=Me, n=1, R$_5$=Et) (compound 6b).

Using the above ethyl 5-(2-amino-1-hydroxypropyl)-2,3-dihydro-2-benzofurancarboxylate as the starting material and adapting method D already described in Example 1c, compound 6b is obtained in a yield of 73%, this compound having the formula

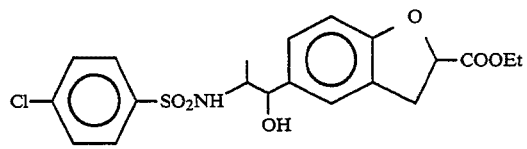

Compound 6b
 empirical formula: $C_{20}H_{22}ClNO_6S$
 molecular weight: 439.91 c) 5-(2-Parachlorobenzenesulphonamido-1-hydroxypropyl)-2,3-dihydro-2-benzofurancarboxylic acid (compound 6).

Starting from the above compound 6b (3.3 mmoles) and using method G (cf. Example 1d), compound 6 is obtained in a yield of 44%, this compound having the formula

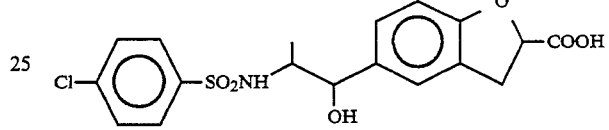

Compound 6
 empirical formula: $C_{18}H_{18}ClNO_6S$
 molecular weight: 411.86
 white crystals
 melting point: 185° C.
 IR (KBr): $\sqrt{}SO_2N$ 1170–1335, $\sqrt{}COOH$ 1710–1735, $\sqrt{}NH$ 3350, $\sqrt{}OH$ 3490 cm$^{-1}$.
 NMR (CDCl$_3$) δ: 0.79, d, 3H, CH$_3$; 4.5, d, 1H, CHOH; 6.43, d, 1H, NH; 7.35, d, 2H, Ar ortho Cl; 7.65, d, 2H, ortho SO$_2$.
 TLC: silica gel 60 Merck F 254
 eluant: chloroform/methanol/acetic acid: 80/18/02
 Rf=0.34
 soluble in DMSO to give a 5% solution.

EXAMPLE 7

6-(2-Parachlorobenzenesulphonoamidoethyl)-2-chromancarboxylic acid I (R=p-ClC$_6$H$_4$—, R$_1$=R$_2$=R$_3$=H, n=1, A=g, X=CH$_2$) (compound 7) (scheme I)

a) Ethyl 6-bromoacetyl-2-chromancarboxylate IV (Y=Br, R$_2$=H, n=1, A=g, R$_5$=Et) (compound 7a).

Using method A according to Example 1a and applying it to 42 mmoles of ethyl 2-chromancarboxylate, compound 7a is obtained in a yield of 83%, this compound having the formula

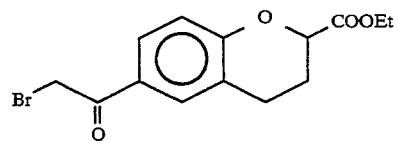

Compound 7a
 empirical formula: $C_{14}H_{15}BrO_4$
 molecular weight: 327.18
 pulverulent white crystals melting point: 89° C.

IR (KBr): √CO 1690, √COOEt 1755 cm$^{-1}$.

NMR (CDCl$_3$) δ: 1.28, t, 3H, C$\underline{H}_3$; 2.15 to 2.30, m, 2H, OCHC$\underline{H}_2$; 2.7 to 2.9, m, 2H, OC$\underline{H}$CH$_2$CH$_2$; 4.25, q, 2H, C$\underline{H}_2$C$\overline{H}_3$; 4.38, s, 2H, Br C$\underline{H}_2$; 4.82, t, 1H, OC$\underline{H}$; 6.98, d, 1H, Ar ortho O; 7.73 to 7.79, m, 2H, Ar ortho CO.

7b) Ethyl 6-(N-ethoxycarbonylparachlorobenzenesulphonamido)acetyl-2-chromancarboxylate XXIV (R=p-ClC$_6$H$_4$—, R$_7$=EtOCO—, R$_2$=H, n=1, A=g, R$_5$=Et) (compound 7b)

Using method I described in Example 2a and 2b and adapting it to the above compound 7a, compound 7b is obtained in a yield of 91%, this compound having the formula

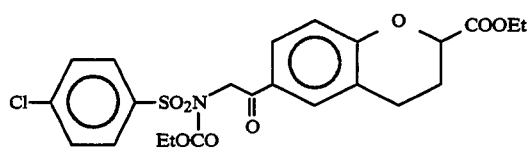

Compound 7b
empirical formula: C$_{23}$H$_{24}$ClNO$_8$S
molecular weight: 509.96
pulverulent white crystals
melting point: 131° C.

IR (KBr): √SO$_2$N 1170–1330, √CO 1690, √COOEt and NCOOEt 1745 cm$^{-1}$.

NMR (CDCl$_3$) δ: 1.12, t, 3H, NCOOCH$_2$C$\underline{H}_3$; 4.11, q, 2H, NCOOC$\underline{H}_2$CH$_3$; 5.28, s, 2H, NC$\underline{H}_2$CO; 7.51, d, 2H, Ar ortho Cl; 8.02, d, 2H, Ar ortho SO$_2$.

7c) 6-(2-Parachlorobenzenesulphonamidoethyl)-2-chromancarboxylic acid (compound 7) XXII (R=p-ClC$_6$H$_4$—, R$_1$=R$_2$=H, n=1, A=g, and for I R$_3$=H, X=CH$_2$).

Adaptation of operating method F described in Example 2c to 9.8 mmoles of ethyl 6-[(N-ethoxycarbonylparachlorobenzenesulphonamido)acetyl]-2-chromancarboxylate enables the compound of formula 7c to be prepared in a quantitative yield, which compound is saponified in the crude form without purification

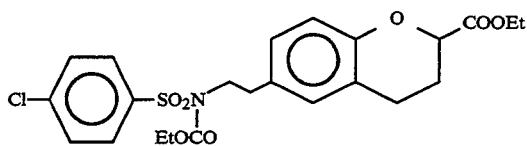

Compound 7c

Compound 7c is treated directly by method G described in Example 2d to give compound 7 in a yield of 35% after recrystallization from ethanol, compound 7 having the formula

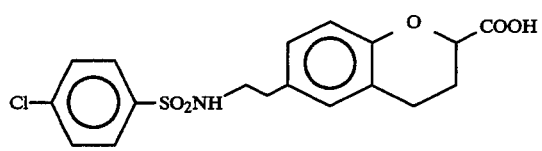

Compound 7
empirical formula: C$_{18}$H$_{18}$ClNO$_5$S
molecular weight: 395.86
white crystals melting point: 142° C.

IR (KBr): √SO$_2$NH 1165–1325, √COOH 1720, √NH 3300 cm$^{-1}$.

NMR (CDCl$_3$) δ: 2.08 to 2.35, m, 2H, OCHC$\underline{H}_2$CH$_2$; 2.63 to 2.78, m, 4H, OCHCH$_2$C$\underline{H}_2$ and ArC$\underline{H}_2$CH$_2$N; 3.14, t, 2H, ArCH$_2$C$\underline{H}_2$N; 4.68, q, 1H, O C$\underline{H}$; 6.74 to 6.86, m, 3H, Ar ortho O and ortho CH$_2$; 7.45, d, 2H, Ar ortho Cl; 7.72, d, 2H, Ar ortho SO$_2$.

TLC: silica gel 60 Merck F 254
eluant: chloroform/methanol/acetic
acid: 80/18/02
Rf: 0.67
soluble in DMSO to give a 20% solution.

EXAMPLE 8

5-(2-Parachlorobenzenesulphonamidoethyl)-1,3-benzodioxole-2-carboxylic acid I (R$_1$=R$_2$=R$_3$=H, n=1, A=c, X=CH$_2$) (scheme I) (compound 8)

8a) Ethyl 5-bromoacetyl-1,3-benzodioxole-2-carboxylate IV (R$_2$=H, n=1, A=c, R$_5$=Et)

Using operating method A described in Example 1a but starting from ethyl 1,3-benzodioxole-2-carboxylate (20.6 mmoles), compound 8a is obtained in a yield of 60%, this compound having the formula

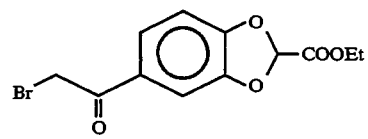

Compound 8a
empirical formula: C$_{12}$H$_{11}$BrO$_5$
molecular weight: 315.124
white crystals
melting point: 50°–51° C.

IR (KBr): √CO 1685, √COOEt 1760 cm$^{-1}$.

NMR (CDCl$_3$) δ: 1.34, t, 3H, C$\underline{H}_3$; 4.32, q, 2H, OC$\underline{H}_2$; 4.37, s, 2H, BrC$\underline{H}_2$; 6.40, s, 1H, C$\underline{H}$; 6.94, d, 2H, Ar ortho O; 7.51, d, 1H and 7.63, dd, 1H, Ar ortho CO.

8b) Ethyl 5-[(N-ethoxycarbonylparachlorobenzenesulphonamido)acetyl]-1,3-benzodioxole-2-carboxylate XXIV (R=p-ClC$_6$H$_4$—, R$_7$—COOEt, R$_2$=H, n=1, A=c, R$_5$=Et) (compound 8b).

Adaptation of method I described in Example 2b to 11 mmoles of ethyl 5-bromoacetyl-1,3-benzodioxole-2-carboxylate enables compound 8b to be prepared in a quantitative yield, this compound having the formula

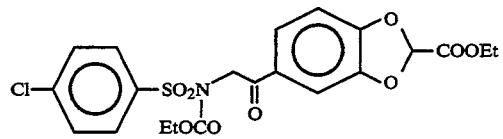

Compound 8b
empirical formula: C$_{21}$H$_{20}$ClNO$_9$S
molecular weight: 497.906
colourless foam NMR (CDCl$_3$) δ: 1.13, t, 3H, C$\underline{H}_3$CH$_2$OCON; 4.12, q, 2H, CH$_3$C$\underline{H}_2$OCON; 5.26, s, 2H, C$\underline{H}_2$N; 7.52, d, 2H, Ar ortho Cl; 8.02, d, 2H, Ar ortho SO$_2$.

8c) 5-(Parachlorobenzenesulphonamidoethyl)-1,3-benzodioxole-2-carboxylic acid (compound 8).

Applying method F described in Example 2c to 11 mmoles of the above derivative 8b, the intermediate 8c is obtained in a quantitative yield, this intermediate having the formula

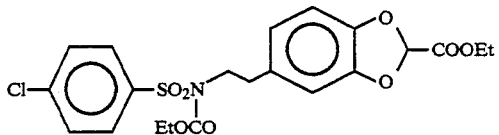

Compound 8c

This derivative is not purified and is used in the crude form to give, by saponification according to method G (cf. Example 2d) and purification in isopropyl ether, compound 8 in a yield of 68%, this compound having the formula

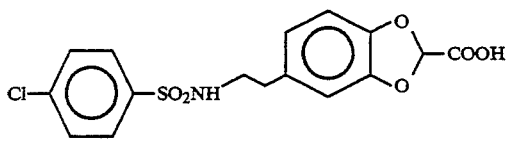

Compound 8
empirical formula: $C_{16}H_{14}ClNO_6S$
molecular weight: 383.806
white crystals
melting point: 138° C.
IR (KBr): $\sqrt{}SO_2N$ 1165–1330, $\sqrt{}COOH$ 1730, $\sqrt{}NH$ 3295 cm$^{-1}$.
NMR (CDCl$_3$) δ: 2.65, t, 2H, ArC$\underline{H_2}$CH$_2$ N; 3.07, t, 2H, ArCH$_2$C$\underline{H_2}$N; 6.24, s, 1H, CH; 6.52 to 6.59, m, 2H, Ar ortho O; 6.71, d, 1H, Ar ortho CH$_2$; 7.42, d, 2H, Ar ortho Cl; 7.70, d, 2H, Ar ortho SO$_2$.
TLC: silica gel 60 Merck F 254
eluant: chloroform/methanol/acetic acid: 80/18/02
Rf: 0.34
soluble in DMSO to give a 20% solution.

EXAMPLE 9

Preparation of 5-(2-parachlorobenzenesulphonamidoethyl)-2-indanecarboxylic acid I ($R_1=R_2=R_3=H$, n=1, X=CH$_2$, A=f) (compound 9) (synthesis scheme I)

a) Methyl 5-bromoacetyl-2-indanecarboxylate.

Using method A described in Example 1a, starting from 17 mmoles of ethyl 2-indanecarboxylate and after purification from isopropyl ether, compound 9a is obtained in a yield of 80%, this compound having the formula

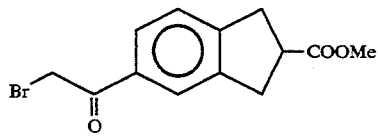

Compound 9a
empirical formula: $C_{13}H_{13}BrO_3$
molecular weight: 297.153
white crystals
melting point: 91° C.

IR (KBr): $\sqrt{}CO$ 1690, $\sqrt{}COOEt$ 1730 cm$^{-1}$.
NMR (CDCl$_3$) δ: 3.27 to 3.41, m, 5H, C$\underline{H_2}$CHC$\underline{H_2}$; 3.74, s, 3H, CH$_3$O; 4.43, s, 2H, BrC$\underline{H_2}$CO; 7.32, d, 1H, Ar meta CO; 7.78 to 7.83, m, 2H, Ar ortho CO.

b) Ethyl 5-[(N-ethoxycarbonylparachlorobenzenesulphonamido)acetyl]-2-indanecarboxylate XXIV (R=p-ClC$_6$H$_4$, R$_7$=EtOCO, n=1, A=f, R$_5$=Et) (compound 9b).

Applying method I described in Example 2b to 13 mmoles of ethyl 5-bromoacetyl-2-indanecarboxylate, compound 9b is obtained in a yield of 94%, this compound having the formula

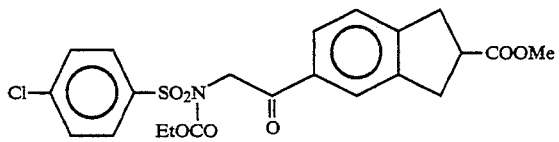

Compound 9b
empirical formula: $C_{22}H_{22}ClNO_7S$
molecular weight: 479.935
white crystals
melting point: 45° C.
IR (KBr): $\sqrt{}SO_2N$ 1185–1330, $\sqrt{}CO$ 1700, $\sqrt{}COOEt$ and NCOOEt 1740 cm$^{-1}$.
NMR (CDCl$_3$) δ: 1.12, t, 3H, C$\underline{H_3}$CH$_2$; 4.13, q, 2H, CH$_3$C$\underline{H_2}$; 5.32, s, 2H, NC$\underline{H_2}$CO; 7.52, d, 2H, Ar ortho Cl; 8.03, d, 2H, Ar ortho SO$_2$.

9c) 5-(2-Parachlorobenzenesulphonamidoethyl)-2-indanecarboxylic acid (compound 9)

Applying method F described in Example 2c to 12 mmoles of the above derivative 9b, the intermediate 9c is obtained in a quantitative yield, this intermediate having the formula

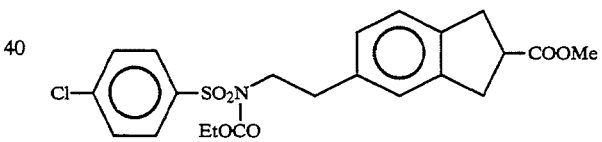

Compound 9c

This derivative is not purified and is used in the crude form to give, after saponification by method G (Example 2d) and after purification from isopropyl ether, compound 9 in a yield of 63%, this compound having the formula

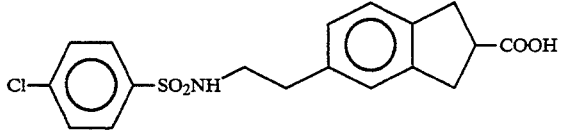

Compound 9
empirical formula: $C_{18}H_{18}ClNO_4S$
molecular weight: 379.862
white crystals
melting point: 140° C.
IR (KBr): $\sqrt{}SO_2N$ 1158–1320, $\sqrt{}COOH$ 1695, $\sqrt{}NH$ 3250 cm$^{-1}$.
NMR (CDCl$_3$): 2.7, t, 2H, ArC$\underline{H_2}$CH$_2$N; 3.03 to 3.32, m, 7H, ArCH$_2$C$\underline{H_2}$N and C$\underline{H_2}$CHC$\underline{H_2}$; 6.82 to 6.89, m, 2H, Ar ortho $\overline{CH_2CH_2N}$; 7.05, d, 1H, Ar meta $CH_2CH_2N$; 7.4, d, 2H, Ar ortho Cl; 7.7, d, 2H, Ar ortho $SO_2$.

TLC: silica gel 60 Merck F 254
eluant: chloroform/methanol/acetic
acid: 90/09/01
Rf: 0.40
soluble in DMSO to give a 10% solution.

EXAMPLE 10

5-(2-Parachlorobenzenesulphonamidoethyl)-2,3-dihydro-2-benzothiophenecarboxylic acid I
($R_1=R_2=R_3=H$, n=1, A=d, X=$CH_2$) (compound 10) (synthesis scheme I)

a) Ethyl 5-bromoacetyl-2,3-dihydro-2-benzothiophenecarboxylate IVa (Y=Br, $R_2$=H, n=1, A=d, $R_5$=Et) (10a).

Using method A according to Example 1a and applying it to 31 mmoles of ethyl 2,3-dihydro-2-benzothiophenecarboxylate and after crystallization from isopropyl ether, compound 10a is obtained in a yield of 81%, this compound having the formula:

Compound 10a
empirical formula: $C_{13}H_{13}BrO_3S$
molecular weight: 329.217
broken white crystals
melting point: 78° C.
IR (KBr): $\sqrt{}$CO 1680, $\sqrt{}$COOEt 1730 cm$^{-1}$.
NMR (CDCl$_3$): 1.28, t, 3H, $CH_3$; 3.45 to 3.81, m, 2H, SCH$CH_2$; 4.2, q, 2H, O$CH_2$; 4.38, s, 2H, Br$CH_2$; 4.49, q, 1H, O$\overline{CH}$CH$_2$; 7.24, d, 1$\overline{H}$, Ar ortho S; 7.73 to 7.80, m, 2H, Ar ortho CO.

10b) Ethyl 5-(N-ethoxycarbonylparachlorobenzenesulphonamidoacetyl)-2,3-dihydro-2-benzothiophenecarboxylate XXIV (R=p-$C_6H_4$—, $R_7$=EtOCO, $R_2$H, n=1, A=d, $R_5$=Et) (compound 7b)

Using method I described in Example 2a and 2b and adapting it to 12 mmoles of the above compound 10a, compound 10b is obtained in a yield of 95% after purification on a silica column and eluting with a 60/20/20 cyclohexane/dichloromethane/acetic acid mixture; this compound is used without further purification and has the formula Compound 10b
empirical formula: $C_{22}H_{22}ClNO_7S_2$
molecular weight: 512.00
yellow viscous oil
IR (film): $\sqrt{}SO_2N$ 1160-1340, $\sqrt{}$CO 1695, $\sqrt{}$COOEt 1730, $\sqrt{}$NCOOEt 1750 cm$^{-1}$.
NMR (CDCl$_3$): 1.12, t, 3H, NCOO$CH_2$CH$_3$; 4.12, q, 2H, NCOOCH$_2$$\overline{CH_3}$; 5.28, s, 2H, N$CH_2$$\overline{CO}$; 7.52, dd, 2H, Ar ortho $\overline{Cl}$; 8.02, dd, 2H, Ar ortho $\overline{SO_2}$.

10c) 5-(2-Parachlorobenzenesulphonamidoethyl)-2,3-dihydro-2-benzothiophenecarboxylic acid XXII (R=p-Cl—$C_6H_4$—, $R_1=R_2$=H, n=1, A=d and for I $R_3$=H and X=$CH_2$) (compound 7)

Adaption of operating method F described in Example 2c to 10.5 mmoles of ethyl 5-[(N-ethoxycarbonylparachlorobenzenesulphonamido)acetyl]-2,3-dihydro-2-benzothiophenecarboxylate enables the compound of formula 10c to be prepared in a quantitative yield; this compound is not purified Compound 10c
This derivative is saponified directly by method G described in Example 2d to give compound 10 in a yield of 60% after recrystallization from isopropyl alcohol, compound 10 having the formula Compound 10
empirical formula: $C_{17}H_{16}ClNO_4S_2$
molecular weight: 397.899
bright yellow crystals
melting point: 152° C.
IR (KBr): $\sqrt{}SO_2N$ 1175-1340, $\sqrt{}$COOH 1720, $\sqrt{}$NH 3290 cm$^{-1}$.
NMR (CDCl$_3$) δ: 2.63, t, 2H, Ar$CH_2$CH$_2$N; 3.03, t, 2H, ArCH$_2$$\overline{CH_2}$N; 3.25 to 3.6, m, 2H, $\overline{SCH}$CH$_2$; 4.36, q, 1H, SCH$\overline{CH_2}$; 6.77 to 6.98, m, 3H, Ar ortho $\overline{CH_2}$ and S; 7.37, d, $\overline{2H}$, Ar ortho Cl; 7.67, d, 2H, Ar ortho $SO_2$.

TLC: silica gel 60 Merck F 254
eluant: chloroform/methanol/acetic
acid: 80/18/02
Rf: 0.62
soluble in DMSO to give a 20% solution.

EXAMPLE 11

5-(Parachlorobenzenesulphonamidoethyl)-2-benzofurancarboxylic acid XXXI (R=p-Cl$C_6H_4$—, $R_1=R_2$=H, n=1, A=b, and for I $R_3$=H and X=$CH_2$) (compound 11) (synthesis scheme III)

a) Ethyl 5-(2-parachlorobenzenesulphonamidoethyl)-2-benzofurancarboxylate XXXIII (R=p-Cl$C_6H_4$—, $R_1=R_2$=H, n=1, A=a) (compound 11a) (method R)

A mixture of 1 g (2.08 mmoles) of ethyl [2-(N -ethoxycarbonylparachlorobenzenesulphonamido)ethyl]-2,3-dihydro-2-benzofurancarboxylate (cf. Example 2c) and 0.41 g (2.28 mmoles) of N-bromosuccinimide in 10 ml of CCl$_4$ is stirred overnight at 25° C. and then heated on an oil bath at 45° C. The orange insoluble matter (succinimide) is filtered off on a glass frit, rinsed with a little CCl$_4$ and removed. The organic phase is evaporated to dryness in a rotary evaporator under vacuum to give compound 11a in a quantitative yield; this compound is not purified

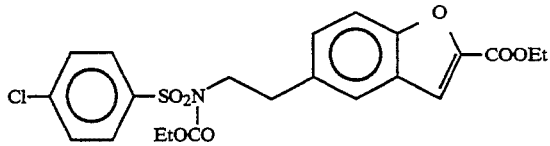

Compound 11a
empirical formula: $C_{22}H_{22}ClNO_7S$
molecular weight: 479.935
viscous amber oil
NMR (CDCl$_3$) δ: 1.17, t, 3H, NCOOCH$_2$C$\underline{H}_3$; 1.44, t, 3H, COOCH$_2$C$\underline{H}_3$; 3.14, t, 2H, ArCH$_2$C$\underline{H}_2$N; 4.04 to 4.16, m, 4H, ArC$\underline{H}_2$CH$_2$N and NCOOC$\underline{H}_2$CH$_3$; 4.44, q, 2H, COOC$\underline{H}_2$CH$_3$; 7.27 to 7.60, m, 6$\underline{H}$, OCCH, Ar ortho O, C$\underline{H}_2$ and Cl; 7.80, d, 2H, Ar ortho SO$_2$.

b) 5-(2-Parachlorobenzenesulphonamidoethyl)-2-benzofurancarboxylic acid (compound 11) (method G)

The above crude derivative 11a is dissolved in 4 ml of dioxane and the solution is then diluted with 2 ml of water and treated with 2.1 ml of 10N sodium hydroxide solution and stirred for 2.5 h at 50° C. and the mixture is treated as described in Example 2d and then purified on a silica (7 g) column eluting with a 950/045/005 chloroform/methanol/acetic acid mixture.

The fractions containing the expected derivative are combined and evaporated to dryness. The residue is recrystallized from isopropanol to give 300 mg (yield=40%) of compound 11 of formula:

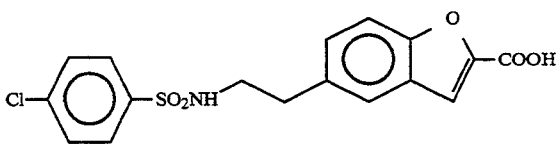

Compound 11
empirical formula: $C_{17}H_{14}ClNO_5S$
molecular weight: 379.818
white crystals
melting point: 195° C.
IR (KBr): $\sqrt{}$SO$_2$N 1180–1345, $\sqrt{}$COOH 1695, $\sqrt{}$NH 3350 cm$^{-1}$.
NMR (CDCl$_3$) δ: 2.82, t, 2H, ArC$\underline{H}_2$CH$_2$N; 3.13, t, 2H, ArCH$_2$C$\underline{H}_2$N; 7.13, d, 1H, Ar ortho O; 7.27 to 7.43, m, 5H, Ar ortho CH$_2$, Cl and OCCH; 7.66, d, 2H, Ar ortho SO$_2$.
TLC: silica gel 60 Merck F 254
eluant: chloroform/methanol/acetic
acid: 80/18/02
Rf: 0.47
Soluble in DMSO to give a 5% solution.

EXAMPLE 12

5-(2-Parachlorobenzenesulphonamidoethyl)-2,3-dihydro-2-benzofurancarboxylic acid XXII (R$_1$=R$_2$=H, R=p-Cl—C$_6$H$_4$, A=a, n=1, and for I R$_3$H, X=CH$_2$((compound 2)

12a) Ethyl 5-(2-bromoethyl)-2,3-dihydro-2-benzofurancarboxylate XIX (R$_2$=H, R$_5$=Et, A=a, n=1)

A solution of 3 g (9.6 mmoles) of ethyl 5-bromoacetyl-2,3-dihydro-2-benzofurancarboxylate (cf. Example 1a) in 22 ml of trifluoroacetic acid is cooled in an ice bath and then treated with 2.45 g (21 mmoles) of triethylsilane added dropwise, at a temperature of between 0° C. and +5° C., and is then allowed to return slowly to normal temperature overnight. The reaction mixture is hydrolysed in 200 ml of crushed ice and extracted with ether. The organic phase is washed with water and with saline water and then dried over sulphate and evaporated to dryness. The two-phase residue (compound 12a+silanols) is rectified under vacuum to give, after the silyl products have passed over at the top, a fraction containing 2.44 g (yield=85%) of pure compound 12a of formula

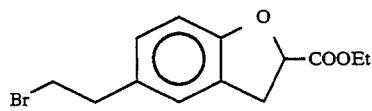

Compound 12a
empirical formula: $C_{13}H_{15}BrO_3$
molecular weight: 299.17
colourless oil
boiling point: 160° C. under 10$^{-3}$ mbars
IR (KBr): $\sqrt{}$COOEt 1760 cm$^{-1}$.
NMR (CDCl$_3$): 1.32, t, 3H, CH$_3$; 3.09, t, 2H, ArCH$_2$C$\underline{H}_2$Br; 3.30 to 3.62, m, 2H, ArC$\underline{H}_2$CHO; 3.52, t, 2H, ArC$\underline{H}_2$CH$_2$Br; 4.27, q, 2H, OC$\underline{H}_2$; 5.2, q, 1H, ArCH$_2$C$\underline{H}$O; 6.84, d, 1H, Ar ortho O; 6.97 to 7.03, m, 2H, Ar ortho CH$_2$.

12b) Ethyl 5-(2-(N-ethoxycarbonylparachlorobenzenesulphonamido)ethyl)-2,3-dihydro-2-benzofurancarboxylate XXI (R=p-Cl—C$_6$H$_4$, R$_7$=COOEt, R$_2$=H, n=1, A=a) (compound 2c).

Using method I described in Example 2 to prepare the intermediate 2b and starting from 1.5 g (5 mmoles) of ethyl 5-(2-bromoethyl)-2,3-dihydro-2-benzofurancarboxylate (compound 12a), compound 2c is obtained in a quantitative yield, this compound having the formula:

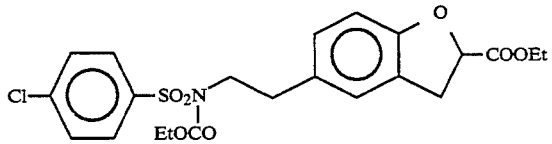

Compound 2c

The characteristics of this compound have already been reported in Example 2 and it is used in the crude state in the following step. The saponification is carried out as in Example 2 to give compound 2 already described and having the same physicochemical properties.

EXAMPLE 13

Preparation of 5-(2-parachlorobenzenesulphonamido-1-hydroxyaminoethyl)-2,3-dihydro-2-benzofurancarboxylic acid XI (R=p-Cl—C$_6$H$_4$, R$_2$=H, R$_4$=H, A=a, n=1, and for I R$_1$=R$_3$=H, X=C=N—OR$_4$) (compound 13) (method H) (synthesis scheme I)

A solution of 1 g (2.5 mmoles) of 5-(parachlorobenzenesulphonamidoacetyl)-2,3-dihydro-2-benzofurancarboxylic acid (cf. Example 1) in 10 ml of pyridine is treated with 0.26 g (2.75 mmoles) of hydroxylamine hydrochloride and stirred for 20 h at 25° C. The mixture is evaporated to dryness under vacuum, the residue is taken up in toluene, the solution is again evaporated and the residue is then dissolved in ethyl acetate and the solution is washed with water and with a dilute citric acid solution and then treated with a dilute solution of sodium bicarbonate so as to obtain a final pH of 5 and finally is washed with a solution of saline water. The organic phase is dried over sulphate and evaporated to dryness and the residue is triturated in isopropyl ether to give 700 mg (yield=68%) of compound 13 of formula:

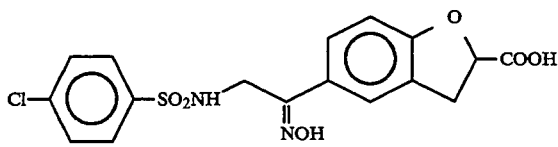

Compound 13
empirical formula: $C_{17}H_{15}ClN_2O_6S$
molecular weight: 410.832
light yellow amorphous powder
melting point slow from 90° C.
IR (KBr): $\sqrt{}SO_2NH$ 1170–1335, $\sqrt{}C=N$ 1595, $\sqrt{}COOH$ 1730, $\sqrt{}NH$ 3300 cm$^{-1}$.
NMR (CDCl$_3$) δ: 3.74 and 3.93, 2s, 2H, N$\underline{CH_2}$; 7.49 and 7.63, 2d, 2H, Ar ortho SO$_2$.
TLC: silica gel 60 Merck F 254
eluant: chloroform/methanol/acetic acid: 80/18/02
Rf: 0.32
soluble in DMSO to give a 10% solution.

EXAMPLE 14

Preparation of 5-(2-parachlorobenzenesulphonamido-1-methoxyiminoethyl)-2,3-dihydro-2-benzofurancarboxylic acid XI (R=p-Cl—C$_6$H$_4$, R$_2$=H, R$_4$=Me, A=a, n=1, and for I R$_1$=R$_3$=H, X=C=N=OR$_4$) (compound 14) (synthesis scheme I)

Using the same method as that described in Example 13 on an identical molar fraction but starting from O-methylhydroxylamine hydrochloride (310 mg; 3.8 mmoles), compound 14 is obtained in a yield of 66%, this compound having the formula:

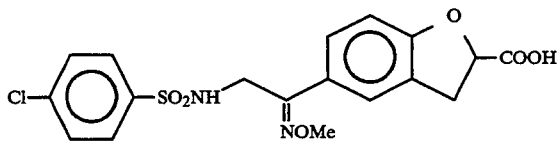

Compound 14
empirical formula: $C_{18}H_{17}ClN_2O_6S$
molecular weight: 424.859
bright yellow amorphous powder
melting point slow from 64° C.
IR (KBr): $\sqrt{}SO_2NH$ 1170–1340; $\sqrt{}C=N$ 1590; $\sqrt{}COOH$ 1740; $\sqrt{}NH$ 3300 cm$^{-1}$.
NMR (CDCl$_3$) δ: 3.70 and 3.90, 2s, 3H, OC$\underline{H_3}$; 4 and 4.12, 2d, 2H, N C$\underline{H_2}$; 5.56 and 5.67, 2t, 1H, N$\underline{H}$.
TLC: silica gel 60 Merck F 254
eluant: chloroform/methanol/acetic acid: 80/18/02
Rf: 0.48
soluble in DMSO to give a 10% solution.

EXAMPLE 15

Preparation of ethyl 5-(parachlorobenzenesulphonamidoacetyl)-2,3-dihydro-2-benzofurancarboxylate VIII (R=p-Cl—C$_6$H$_4$, R$_2$=H, R$_5$=Et, A=a, n=1, and for I R$_1$=H, R$_3$=Et, X=CO) (compound 1d) (method K) (synthesis scheme I)

A mixture of 3.95 g (10 mmoles) of 5-(parachlorobenzenesulphonamidoacetyl)-2,3-dihydro-2-benzofurancarboxylic acid (cf. Example 1) in 30 ml of anhydrous ethanol and containing 0.2 ml of concentrated sulphuric acid is heated under reflux for 2 hours and then, after the temperature has returned to 25° C., the mixture is evaporated to dryness in a rotary evaporator under vacuum. The residue is taken up in ethyl acetate and the solution is washed with water and with a dilute solution of sodium bicarbonate and then with water and with saline water. The organic phase is dried over sodium sulphate and evaporated to dryness and the residue is triturated in isopropyl ether to give compound 1d in a yield of 85%, this compound having the formula:

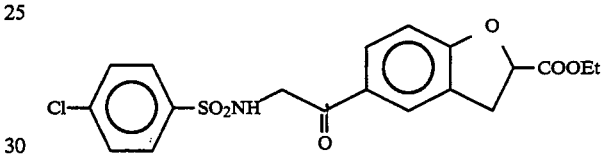

Compound 1d
The physicochemical characteristics of this compound have already been reported in Example 1.

EXAMPLE 16

Preparation of 5-(N-methylparatoluenesulphonamidoacetyl)-2,3-dihydro-2-benzofurancarboxylic acid XXV (R=p-Me-C$_6$H$_4$, R$_7$=Me, R$_2$=H, A=a, n=1, and for I R$_1$=Me, X=CO) (compound 16)

a) Ethyl 5-(N-methylparatoluenesulphonamidoacetyl)-2,3-dihydro-2-benzofurancarboxylate (16a). Using method I described in Example 2b but applying it to the sodium salt of N-methyl-paratoluenesulphonamide (1 g; 5.4 mmoles) and subjecting it to a condensation reaction with 1.7 g (5.4 mmoles) of ethyl 5-bromoacetyl-2,3-dihydro-2-benzofurancarboxylate, compound 16a is obtained in a quantitative yield, this compound having the formula

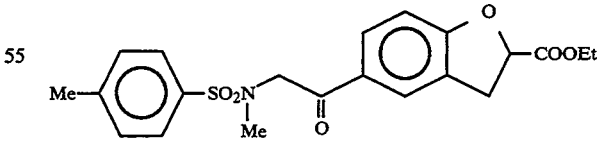

Compound 16a
empirical formula: $C_{20}H_{23}NO_6S$
molecular weight: 405.461
whitish foam which is not isolated.

b) Saponification of compound 16a to derivative 16 (method G). The above crude ester 16a is saponified by method G described in Example 1e to give 1.1 g (yield=52%) of compound 16 after purification on a silica (20 g) column and elution with a 950/045/005 chloroform/methanol/acetic acid mixture, compound 16 having the formula

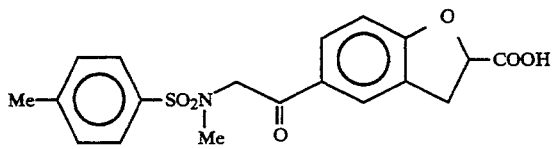

Compound 16
 empirical formula: $C_{19}H_{19}NO_6S$
 molecular weight: 389.426
 white crystals
 melting point: 149° C.
 IR (KBr): $\sqrt{}SO_2N$ 1160–1335, $\sqrt{}CO$ 1680, $\sqrt{}COOH$ 1740 cm$^{-1}$.
 NMR (CDCl$_3$) δ: 2.39, s, 3H, MeN; 2.74, s, 3H, MeAr; 3.30 to 3.63, m, 2H, OCHCH$_2$; 4.4, s, 2H, NCH$_2$CO; 5.22, q, 1H, OCHCH$_2$; 6.87, d, 1H, Ar ortho O; 7.28, d, 2H, Ar ortho CH$_3$; 7.65, d, 2H, Ar ortho SO$_2$; 7.8, m, 2H, Ar ortho CO.
 TLC: silica gel 60 Merck F 254
 eluant: chloroform/methanol/acetic acid: 80/18/02
 Rf: 0.56
 soluble in DMSO to give a 10% solution.

EXAMPLE 17

Sodium 5-(2-parachlorobenzenesulphonamidoethyl)-2,3-dihydro-2-benzofurancarboxylate I (R=p-Cl—C$_6$H$_4$, R$_1$=R$_2$=H, R$_3$=Na, n=1, X=CH$_2$, A=a) (compound 17)

A mixture of 1 g (2.6 mmoles) of 5-(2-parachlorobenzenesulphonamidoethyl)-2,3-dihydro-2-benzofurancarboxylic acid (compound 2, Example 2) in 10 ml of RP ethanol is cooled in an ice bath and then treated with a stoichiometric amount (+10% excess) of a solution of sodium methylate, added dropwise. After stirring for 15 min, the mixture is brought to 50° C. on an oil bath for 15 min, and after leaving to stand overnight, the insoluble sodium salt is filtered off to give compound 17 in a yield of 80%, this compound having the formula

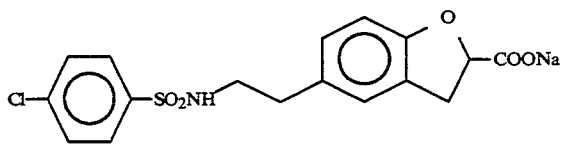

Compound 17
 empirical formula: $C_{17}H_{15}ClNNaO_5S$
 molecular weight: 403.816
 white crystals
 melting point: >280° C.
 IR (KBr): $\sqrt{}COONa$ 1620 cm$^{-1}$.
 soluble in water to give a 1.5% solution.

EXAMPLE 18

5-(Parachlorobenzenesulphonamidoacetyl)-2,3-dihydrobenzofurancarboxylic acid XXV (R=p-Cl—C$_6$H$_4$, R$_1$=R$_2$=H, n=1, A=a and for I X=CO, R$_3$=4) (compound 1) (method P, synthesis scheme I).

a) Sodium salt of N-tert.-butoxycarbonyl-parachlorobenzenesulphonamide XX (R=p-Cl—C$_6$H$_4$, R$_7$=t-BuOCO, Na salt), compound 18a.

Using the operating method described in Example 2a but subjecting 11.4 g (52 mmoles) of di-tert.-butylpyrocarbonate to a condensation reaction with 5 g (26 mmoles) of parachlorobenzenesulphonamide, the compound of formula

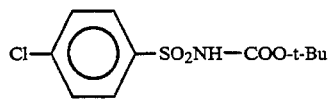

is obtained in a yield of 70% after purification from cyclohexane.
 empirical formula: $C_{11}H_{14}ClNO_4S$
 molecular weight: 291.753
 white crystals
 melting point: 128° C.
 IR (KBr): $\sqrt{}SO_2N$ 1170–1345; $\sqrt{}COO$ 1740; $\sqrt{}NH$ 3270 cm$^{-1}$.

The sodium salt of this compound is prepared starting from 2 g (6.9 mmoles) of the above compound using operating method 2a to give compound 18a in a yield of 85%, this compound having the formula

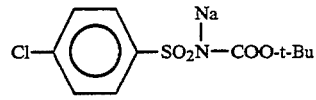

Compound 18a
 empirical formula: $C_{11}H_{13}ClNNaO_4S$
 molecular weight: 313.746
 white crystals
 instantaneous melting point 210°–215° C. with decomposition
 IR (KBr): $\sqrt{}NCOO$ 1640 cm$^{-1}$.

18b) Ethyl 5-(N-tert.-butoxycarbonyl-parachlorobenzenesulphonamidoacetyl)-2,3-dihydro-2-benzofurancarboxylate XXIV (R=p-Cl—C$_6$H$_4$, R$_7$=COOtBu, R$_2$=H, n=1, A=a, R$_5$=Et) (compound 18b)

Starting from 1 g (3.2 mmoles) of the sodium salt of N-tert.-butoxycarbonyl-parachlorobenzenesulphonamide and subjecting this to a condensation reaction with 0.90 g (2.85 mmoles) of ethyl 5-bromoacetyl-2,3-dihydro-2-benzofurancarboxylate (compound 1a) in accordance with the process described in Example 2b, crude compound 18b is obtained in a yield of 90%, this compound having the formula:

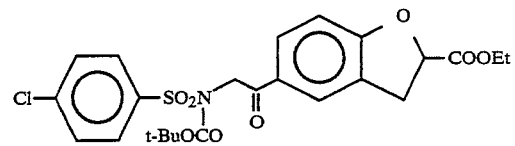

Compound 18b empirical formula: $C_{24}H_{26}ClNO_8S$
molecular weight: 523.99
viscous amber oil
NMR (CDCl$_3$) δ: 1.3, s, 9H, (CH$_3$)$_3$C; 3.36, t, 3H, CH$_3$CH$_2$; 3.44 to 3.63, m, 2H, OCHCH$_2$; 4.3, q, 2H, CH$_2$CH$_3$; 5.24, s, 2H, NCH$_2$; 5.31, q, 1H, OCH; 6.98, d, 1H, Ar ortho O; 7.52, d, 2H, Ar ortho Cl; 7.85, m, 2H, Ar ortho CO; 8.07, d, 2H, Ar ortho SO$_2$.

18c) Ethyl 5-(parachlorobenzenesulphonamidoacetyl)-2,3-dihydro-2-benzofurancarboxylate XXV (R=p-R$_1$=R$_2$=H, n=1, A=a, R$_3$=Et) (method P)

A solution of 500 mg (0.95 mmoles) of the above compound 18b in 20 ml of ethyl acetate containing 2 moles of gaseous HCl per liter is stirred for 2 h at 25° C. and then evaporated to dryness. The residue is taken up in isopropyl ether and the insoluble matter is recovered (weight=0.32 g-yield=77%) and has the formula

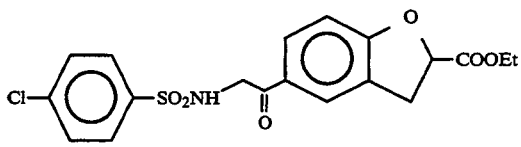

Compound 1d

The physicochemical characteristics of this derivative have already been reported in Example 1. It can be saponified by method G to give compound 1.

EXAMPLE 19

Preparation of ethyl 5-(2-(N-ethoxycarbonylparachlorobenzenesulphonamido)ethyl)-2,3-dihydro-2-benzofurancarboxylate XXI (R=p-Cl—C$_6$H$_4$, R$_7$=EtOCO, R$_2$=H, R$_5$=Et, n=1) (compound 2c) (method M) (synthesis scheme I)

A mixture of 1 g (2.02 mmoles) of ethyl 5-(N-ethoxycarbonylparachlorobenzenesulphonamidoacetyl)-2,3-dihydro-2-benzofurancarboxylate (cf. compound 2b, Example 2) in 60 ml of acetic acid containing 3 drops of perchloric acid is hydrogenated in a stainless steel reactor under a pressure of 4 bars in the presence of 200 mg of palladium deposited on charcoal (10%) as the catalyst. After stirring for 24 h at 25°C., the reactor is purged with nitrogen, the catalyst is filtered off and the filtrate is poured onto crushed ice, keeping the pH at about 2-3 by adding a saturated solution of sodium bicarbonate. The mixture is extracted with ethyl acetate and the extract is washed with a dilute solution of sodium bicarbonate and then with water and with saline water and dried over sulphate. The residue (920 mg) is purified on a silica (20 g) column eluting with an 85/15 hexane/ethyl acetate mixture. The fractions containing the expected derivative are combined and evaporated to dryness to give 700 mg (yield=72%) of compound 2c in the form of a slightly yellow coloured viscous oil of formula

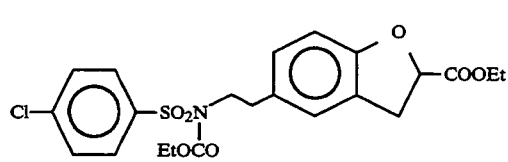

Compound 2c

The physicochemical characteristics (IR and NMR spectra) of this compound have already been given in Example 2.

EXAMPLE 20

Preparation of ethyl 6-(parachlorobenzenesulphonamidoacetyl)-2-chromancarboxylate XXV (R=p-Cl—C$_6$H$_4$, R$_1$=R$_2$=H, R$_3$=Et, n=1, A=g and for I X=CO) (compound 20) (synthesis scheme I)

20a) Ethyl 6-(N-tert.-butyloxycarbonyl-parachlorobenzenesulphonamidoacetyl)-2-chromancarboxylate XXIV (R=p-Cl—C$_6$H$_4$, R$_7$=COO-tBu, R$_2$=H, R$_5$=Et, n=1, A=g) (compound 20a) (method I).

Using the sodium salt of N-tert.-butyloxycarbonyl-parachlorobenzenesulphonamide XX (R=p-Cl—C$_6$H$_4$, R$_7$=t-BuOCO—) prepared according to Example 18a and subjecting 5.51 g (17.5 mmoles) of this compound to a condensation reaction with 5 g (15.2 mmoles) of ethyl 5-bromoacetyl-2-chromancarboxylate in accordance with the process described in Example 18b, compound 20a is obtained in a yield of 99%; this compound is used in the crude form in the following step and has the formula

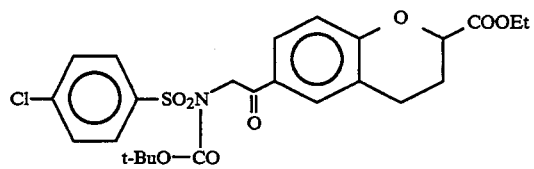

Compound 20a
empirical formula: $C_{25}H_{28}ClNO_8S$
molecular weight: 523.99
broken white powder
melting point slow: 60° C.

IR (KBr): √SO$_2$ 1170-1350; √CO 1700; √COOEt and NCOOtBu 1755 cm$^{-1}$.

NMR (CDCl$_3$) δ: 1.3, m, 12H, C(CH$_3$)$_3$, OCH$_2$CH$_3$; 3.40, q, 1H, OCHCH$_2$Ar; 3.63, q, 1H, OCHCH$_2$Ar; 4.28, q, 2H, OCH$_2$CH$_3$; 5.3, m, 3H, OCHCH$_2$Ar, NHCH$_2$CO; 6.97, d, 1H, Ar ortho O; 7.52, d, 2H, Ar ortho Cl; 7.84, m, 2H, Ar ortho CO; 8.03, d, 2H, Ar ortho SO$_2$.

20b) Ethyl 6-parachlorobenzenesulphonamidoacetyl-2-chromancarboxylate XXV (R=p-Cl—C$_6$H$_4$, R$_1$=R$_2$=H, R$_3$=Et, A=g, n=1) (compound 20) (method P).

By treating 8.2 g (15.2 mmoles) of the above compound 20a in the presence of 100 ml of ethyl acetate containing 2 moles of gaseous HCl per liter in accordance with Example 18c, and after recrystallization of the crude residue from 100 ml of a 90/10 isopropanol ether/ethyl acetate mixture, compound 20 is prepared in a yield of 73%, this compound having the formula

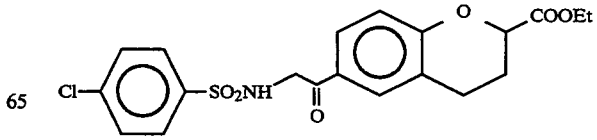

Compound 20 empirical formula: $C_{20}H_{20}ClNO_6S$
molecular weight: 437.90
pulverulent white crystals
melting point: 150° C.
IR (KBr): $\sqrt{}SO_2N$ 1160–1350; $\sqrt{}CO$ 1690; $\sqrt{}COOEt$ 1740, $\sqrt{}NH$ 3300 cm$^{-1}$.

NMR (CDCl$_3$) δ: 1.24, t, 3H, CH$_3$; 2.18, m, 2H, OCHCH$_2$Ar; 2.73, m, 2H, OCHCH$_2$CH$_2$Ar; 4.20, q, 2H, OCH$_2$CH$_3$; 4.35, s, 2H, NHCH$_2$CO; 4.78, t, 1H, OCHCH$_2$CH$_2$Ar; 6.06, s, 1H, NH; 6.90, d, 1H, Ar ortho O; 7.40, d, 2H, Ar ortho Cl; 7.58, m, 2H, Ar ortho CO; 7.79, d, 2H, Ar ortho SO$_2$.

TLC: silica gel 60 Merck F 254
eluant: hexane/ethyl acetate: 50/50
Rf: 0.35
solubility: soluble in DMSO to give a 25% solution insoluble in water.

EXAMPLE 21

Preparation of 6-(parachlorobenzenesulphonamidoacetyl)-2-chromancarboxylic acid IX (R=p-Cl—C$_6$H$_4$, R$_2$=H, n=1, A=g) (compound 21) (synthesis scheme I) (method G)

Starting from 3.9 g (8.9 mmoles) of ethyl 6-parachlorobenzenesulphonamidoacetyl-2-chromancarboxylate (compound 20) and saponifying this ester in accordance with the process described in Example 1e and purifying the product on a column of 20 g of silica/eluant CHCl$_3$/MeOH/AcOH 95/4.4/0.5, compound 21 is prepared with a yield of 40%, this compound having the formula

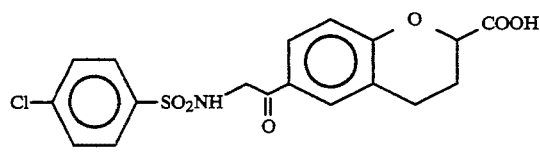

Compound 21
empirical formula: $C_{18}H_{16}ClNO_6S$
molecular weight: 409.84
white crystals
melting point: 174°–175° C.
IR (KBr): $\sqrt{}COOH$ 1740; $\sqrt{}CO$ 1690; $\sqrt{}NH$ 3300 cm$^{-1}$.

NMR (CDCl$_3$) δ: 2.18, m, 2H, OCHCH$_2$CH$_2$Ar; 2.76, m, 2H, OCHCH$_2$CH$_2$Ar; 4.32, s, 2H, NHCH$_2$CO; 4.74, t, 1H, OCHCH$_2$Ar; 6.23, s, 1H, NH; 6.90, d, 1H, Ar ortho O; 7.40, d, 2H, Ar ortho Cl; 7.57, m, 2H, Ar ortho CO; 7.78, d, 2H, Ar ortho SO$_2$.

TLC: silica gel 60 Merck F 254
eluant: chloroform/methanol/acetic acid 80/18/02
Rf: 0.35
solubility: soluble in DMSO to give a 25% solution insoluble in water.

EXAMPLE 22

Preparation of 5-(benzenesulphonamidoacetyl)-2,3-dihydro-2-benzofurancarboxylic acid IX (R=C$_6$H$_5$, R$_2$=H, n=1, A=a) and for I (X=CO, R$_1$=R$_3$=H) (compound 22) (synthesis scheme I).

22a) Ethyl 5-(benzenesulphonamidoacetyl)-2,3-dihydro-2-benzofurancarboxylate VII (compound 22a) (R=C$_6$H$_5$, R$_2$=H, A=a, R$_5$=Et) (method D)

Treating 3 g (10.4 mmoles) of ethyl 5-(aminoacetyl)-2,3-dihydro-2-benzofurancarboxylate hydrochloride (compound 1c) with 2.8 g (15.7 mmoles) of benzenesulphonyl chloride in accordance with operating method 1d, compound 22a is obtained in a yield of 75% after recrystallization from isopropyl alcohol; this compound has the formula

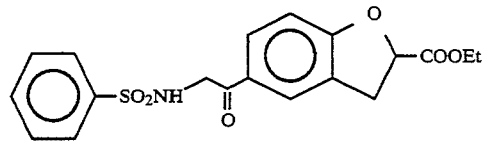

Compound 22a
empirical formula: $C_{19}H_{19}NO_6S$
molecular weight: 389.43
broken white crystals
melting point: 109° C.
NMR (CDCl$_3$) δ: 1.30, t, 3H, OCH$_2$CH$_3$; 3.53, q, 1H, OCHCH$_2$Ar; 3.81, q, 1H, OCHCH$_2$Ar; 4.27, q, 2H, OCH$_2$CH$_3$; 4.63, d, 2H, NHCH$_2$CO; 5.93, q, 1H, OCHCH$_2$Ar; 6.71, t, 1H, NH; 7.01, d, 1H, Ar ortho O; 7.62 to 8.10, m, 7H, Ar.

22b) 5-Benzenesulphonamidoacetyl-2,3-dihydro-2-benzofurancarboxylic acid IX (compound 22) (R=C$_6$H$_5$, R$_2$=H, n=1, A=a) (method G)

Carrying out the reaction as in Example 1e but starting from 2.95 g (7.57 mmoles) of the above ester 22a, compound 22 is obtained in a yield of 40% after purification on a silica column; this compound has the formula

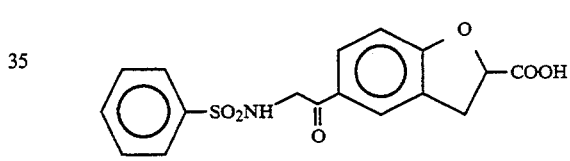

Compound 22
empirical formula: $C_{17}H_{15}NO_6S$
molecular weight: 361.37
broken white crystals
melting point: 179° C.
IR (KBr): $\sqrt{}SO_2$ 1180–1346; $\sqrt{}CO$ 1690; $\sqrt{}COOH$ 1750; $\sqrt{}NH$ 3300 cm$^{-1}$ NMR (CDCl$_3$) δ: 3.53, q, 1H, OCHCH$_2$Ar; 3.81, q, 1H, OCHCH$_2$Ar; 4.63, d, 2H, NHCH$_2$CO; 5.93, q, 1H, OCHCH$_2$Ar; 6.71, t, 1H, NH; 7.01, d, 1H, Ar ortho O; 7.62 to 8.10, m, 7H, Ar.

TLC: silica gel 60 Merck F 254
eluant: chloroform/methanol/acetic acid 80/18/02
Rf: 0.30
solubility: soluble in DMSO to give a 25% solution insoluble in water.

EXAMPLE 23

Preparation of 5-paramethoxybenzenesulphonamidoacetyl-2,3-dihydro-2-benzofurancarboxylic acid IX (R=p-CH$_3$O—C$_6$H$_4$—, R$_2$=H, n=1, A=a) and for I (R$_1$=R$_3$=H and X=CO) (compound 23) (synthesis scheme I) (method D)

23a) Ethyl 5-paramethoxybenzenesulphonamidoacetyl-2,3-dihydro-2-benzofurancarboxylate VIII (compound 23a) (R=p-CH$_3$O—C$_6$H$_4$—, R$_2$=H, A=a, R$_5$=Et, n=1)

Reacting 3 g (10.4 mmoles) of ethyl 5-aminoacetyl-2,3-dihydro-2-benzofurancarboxylate hydrochloride (compound 1c) with 3 g (14.5 mmoles) of paramethoxybenzenesulphonyl chloride in accordance with the process described in Example 1d, compound 23a is obtained quantitatively, this compound having the formula

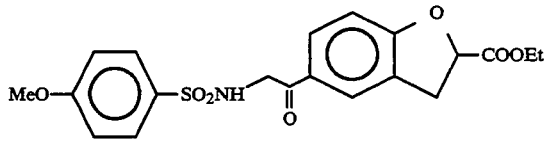

Compound 23a
  empirical formula: $C_{20}H_{21}NO_7S$
  molecular weight: 421.46
  amber viscous oil 23b) 5-Paramethoxybenzenesulphonamidoacetyl-2,3-dihydro-2-benzofurancarboxylic acid IX (compound 23) (R=p-CH$_3$O—C$_6$H$_4$—, R$_2$=H, n=1, A=a) (method G)

Carrying out the reaction in the same way as in Example 1e but starting from 4.42 g (10.4 mmoles) of the above crude ester (compound 23a), compound 23 is obtained in a yield of 35% after recrystallization from chloroform; this compound has the formula

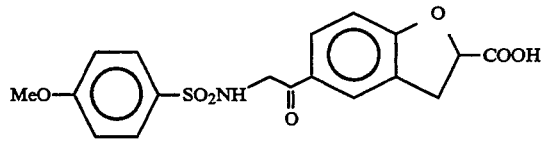

Compound 23
  empirical formula: $C_{18}H_{17}NO_7S$
  molecular weight: 391.40
  white crystals
  melting point: 162° C.
  IR (KBr): $\sqrt{}$SO$_2$ 1160–1350; $\sqrt{}$CO 1695; $\sqrt{}$COOH 1755; $\sqrt{}$NH 3300 cm$^{-1}$ NMR (CDCl$_3$) δ: 6.95, m, 3H, Ar ortho O; 7.65 to 7.75, m, 4H, Ar.
  TLC: silica gel 60 Merck F 254
  eluant: chloroform/methanol/acetic acid 80/18/02
  Rf: 0.30
  solubility: soluble in DMSO to give a 30% solution

EXAMPLE 24

5-(Pentafluorobenzenesulphonamidoacetyl)-2,3-dihydro-2-benzofurancarboxylic acid IX (R=C$_6$F$_5$, R$_2$=H, n=1, A=a) and for I (X=CO, R$_1$=R$_3$=H) (compound 24) (synthesis scheme I) (method D)

24a) Ethyl 5-(pentafluorobenzenesulphonamidoacetyl)-2,3-dihydro-2-benzofurancarboxylate VIII (R=C$_6$F$_5$, R$_2$=H, n=1, R$_5$=Et, A=a).

Starting from 3 g (10.4 mmoles) of ethyl 5-(aminoacetyl)-2,3-dihydro-2-benzofurancarboxylate hydrochloride (compound 1c) and subjecting this to a condensation reaction in accordance with Example 1d with 4 g (15 mmoles) of pentafluorobenzenesulphonyl chloride, 1.30 g (yield 26%) of compound 24a are obtained after purification on silica and crystallization from isopropyl ether; this compound has the formula

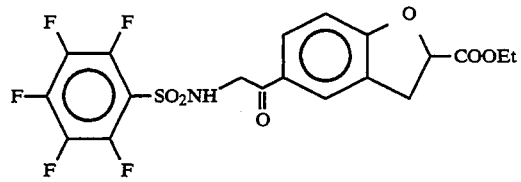

Compound 24a
  empirical formula: $C_{19}H_{14}F_5NO_6S$
  molecular weight: 479.38
  yellow crystals
  melting point: 127° C.

24b) 5-Pentafluorobenzenesulphonamidoacetyl-2,3-dihydro-2-benzofurancarboxylic acid (compound 24)

A solution of 1.1 g (2.3 mmoles) of the above ester in a methanol/water mixture containing sodium bicarbonate is saponified in accordance with the process described in Example 1e to give 0.55 g (yield 58%) of compound 24 after purification on silica and crystallization from isopropyl ether; this compound has the formula

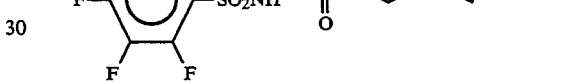

Compound 24
  empirical formula: $C_{17}H_{10}F_5NO_6S$
  molecular weight: 451.32
  broken white crystals
  melting point: 200° C. instantaneous
  IR (KBr): $\sqrt{}$SO$_2$ 1180–1330; $\sqrt{}$CO 1690; $\sqrt{}$COOH 1735; $\sqrt{}$NH 3240 cm$^{-1}$
  NMR (CDCl$_3$) δ: 3.54, q, 1H, OCHCH$_2$Ar; 3.82, q, 1H, OCHCH$_2$Ar; 4.93, s, 2H, NHCH$_2$CO; 5.54, q, 1H, OCHCH$_2$Ar; 7.04, d, 1H, Ar ortho $\overline{O}$; 7.73, s, 1H, NH; 7.$\overline{98}$, m, 2H, Ar ortho CO.
  TLC: silica gel 60 Merck F 254
  eluant: chloroform/methanol/acetic acid 80/18/02
  Rf: 0.42
  solubility: soluble in DMSO to give a 20% solution insoluble in water.

EXAMPLE 25

(dl)-Lysine 5-parachlorobenzenesulphonamidoacetyl-2,3-dihydro-2-benzofurancarboxylate trihydrate I (R=p-Cl—C$_6$H$_4$—, R$_1$=R$_2$=R$_3$=H, n=1, A=a, X=CO)

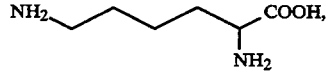

3H$_2$O) (compound 25)

A 50% solution of 6.65 g (22.7 mmoles) of dl-lysine is diluted with 18 ml of water and then treated at 20° C. with 6.65 g (16.8 mmoles) of 5-parachlorobenzenesulphonamidoacetyl-2,3-dihydro-2-benzofurancarboxylic acid (compound 1). The mixture becomes homogeneous and the salt then crystallizes. The crystallization is completed by adding 150 ml of isopropyl alcohol. After stirring for a further 1 hour, the salt is filtered off, drained and dried and then recrystallized from 300 ml of a 75/25 alcohol/water mixture to give compound 25 in a yield of 70%, this compound having the formula

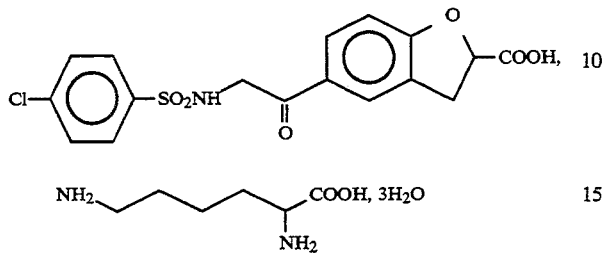

Compound 25
 empirical formula: $C_{23}H_{34}ClN_3O_{11}S$
 molecular weight: 596.05
 broken white crystals
 melting point slow: 130° C.
 IR (KBr): $\sqrt{SO_2}$ 1173–1335–1360; $\sqrt{CO}$, $COO^-$ wide band centred on 1600, $\sqrt{NH}$ 3300 cm$^{-1}$
 solubility: soluble in water to give a 1% solution.

EXAMPLE 26

(dl)-Lysine 6-(2-parachlorobenzenesulphonamidoethyl)-2-chromancarboxylate I (R=p-Cl—C$_6$H$_4$—, R$_1$=R$_2$=R$_3$=H, n=1, A=g, X=CH$_2$)

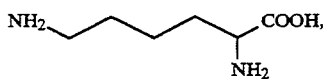

(compound 26)

Carrying out the reaction in the same way as for the process described in Example 25 but starting from 3.45 g (8.7 mmoles) of 6-(2-parachlorobenzenesulphonamidoethyl)-2-chromancarboxylic acid, compound 26 is obtained directly (without recrystallization) in a yield of 95%, this compound having the formula

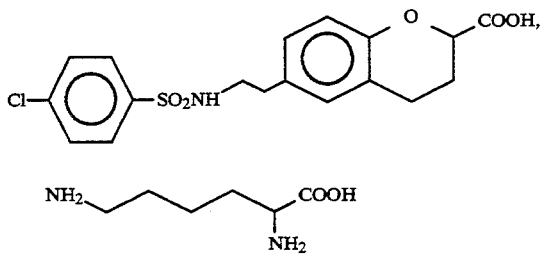

Compound 26
 empirical formula: $C_{24}H_{32}ClN_3O_7S$
 molecular weight: 542.05
 white crystals
 melting point: 214° C.
 IR (KBr): $\sqrt{SO_2}$ 1180–1330–1355; $\sqrt{CO}$, $COO^-$ wide band centred on 1600
 solubility: soluble in water to give a 1% solution.

EXAMPLE 27 dl-Lysine 6-(parachlorobenzenesulphonamidoacetyl)-2-chromancarboxylate I (R=p-Cl—C$_6$H$_4$—, R$_1$=R$_2$=R$_3$=H, n=1, A=g, X=CO),

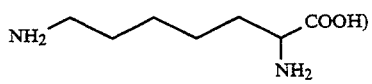

(compound 26)

Carrying out the reaction as described in Example 25 but starting from 4.45 g (10.8 mmoles) of 6-(2-parachlorobenzenesulphonamidoethyl)-2-chromancarboxylic acid and 4.28 g of a 50% solution of dl-lysine in water, compound 27 is obtained directly in a yield of 92%, this compound having the formula

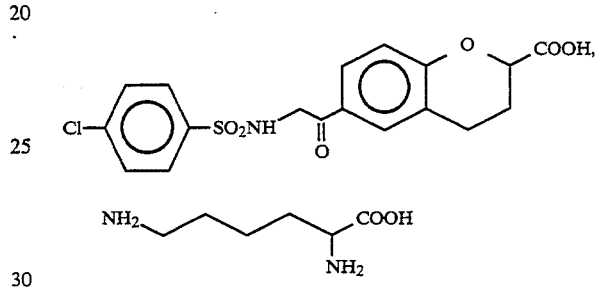

Compound 27
 empirical formula: $C_{24}H_{30}ClN_3O_8S$
 molecular weight: 556.034
 broken white crystals
 melting point: 226° C.
 IR (KBr); $\sqrt{SO_2}$ 1180–1330–1355; $\sqrt{CO}$, $COO^-$ wide band centred on 1610 cm$^{-1}$
 solubility: soluble in water to give a 1% solution.

EXAMPLE 28

5-(Parachlorobenzenesulphonamidoacetyl)-2-indanecarboxylic acid I (R=p-Cl—C$_6$H$_4$—, R$_1$=R$_2$=R$_3$=H, n=1, A=f, X=CO) (compound 28) (modified method P)

Using the operating method of Example 18a but starting from 15 g (50.5 mmoles) of ethyl 5-bromoacetyl-2-indanecarboxylate prepared in accordance with 9a and subjecting this to a condensation reaction with 17.4 g (55 mmoles) of the sodium salt of N-tert.-butyloxycarbonyl-parachlorobenzenesulphonamide prepared in accordance with 18a, the synthesis intermediate of formula

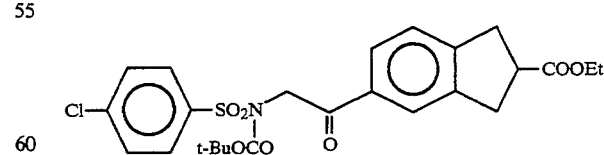

is obtained in a quantitative yield; this intermediate is not isolated and is hydrolysed for 1 h at 60° C. with 250 ml of an aqueous solution of concentrated hydrochloric acid.

This reaction mixture is diluted with 600 ml of water and the precipitate formed is filtered off, drained, washed with water, dried and recrystallized from boiling ethyl acetate to give 6 g (yield=70%) of white crystals of formula

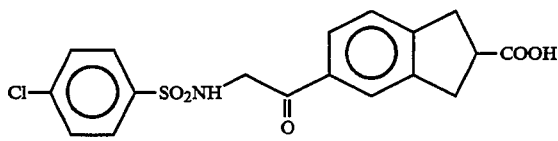

Compound 28
empirical formula: $C_{18}H_{16}ClNSO_6$
molecular weight: 393.845
white crystals
melting point: 150° C. then recrystallizes and remelts at 181° C.
IR (KBr): $\sqrt{}SO_2$ 1163–1350; $\sqrt{}CO$ and COOH 1700; $\sqrt{}NH$ 3290 cm$^{-1}$
NMR (DMSO d$_6$): from 3.1 to 3.35, m, 5H, CH$_2$CHCH$_2$; 4.48, d, 2H, NCH$_2$CO; 7.34, d, 1H, Ar meta of CO; 7.64, d, 2H, Ar ortho Cl; 7.84, d, 2H, Ar ortho SO$_2$; 7.6 to 7.8, m, 2H, Ar ortho CO; 8.18, t, 1H, NH; 12.4, s, 1H, COOH.
TLC: silica gel Merck F 254
eluant: chloroform/methanol/acetic acid: 90/09/01
Rf=0.46
insoluble in water; soluble in DMSO to give a 15% solution.

EXAMPLE 29 dl-Lysine 5-(parachlorobenzenesulphonamidoacetyl)-2-indanecarboxylate I (R=p-Cl—C$_6$H$_4$—, R$_1$=R$_2$=R$_3$=H, n=1, A=f, X=CO),

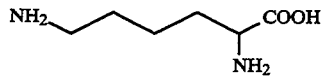

(compound 29)

Carrying out the reaction as described in Example 25 but starting from 5 g (12.5 mmoles) of 5-(parachlorobenzenesulphonamidoacetyl)-2-indanecarboxylic acid and 3.42 g of a 50% aqueous solution of lysine, 6 g of crude salt are obtained which are recrystallized from a 60/40 ethanol/water solution to give compound 29 in a yield of 66%, this compound having the formula

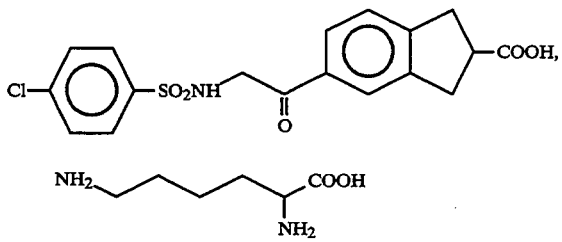

Compound 29
empirical formula: $C_{24}H_{30}ClN_3O_7S$
molecular weight: 540.035
broken white crystals
melting point with decomposition: 165° C.
IR (KBr): $\sqrt{}SO_2$ 1160–1350; $\sqrt{}CO$ 1690; $\sqrt{}NH$ 3300 cm$^{-1}$
soluble in water to give a 0.5% solution.

BIOLOGICAL EXPERIMENTS

The compounds of the present invention of general formula I and their therapeutically acceptable acid salts have valuable pharmacodynamic properties. These compounds are highly anti-aggregant by selective inhibition of the action of thromboxane A$_2$. These compounds are active both at the platelet level and at the endothelial tissue level. These compounds oppose the platelet aggregation induced by the thromboxamimetic compound U.46619 and the platelet aggregation induced by arachidonic acid. This action is revealed in in vitro or ex vivo tests. These compounds can be used for preventive purposes in cardiovascular ischaemia and as adjuvant treatment for thromboses or in myocardial infarction.

1) Toxicology

The chemical compounds described above were subjected to toxicity checks. This study was carried out on conventional mice weighing from 20 to 22 g. The compounds of general formula I were administered intraperitoneally. At 500 mg per kilo, compounds 1, 2 and 3, given by way of non-limiting example, proved to be atoxic and not a single fatality is observed at this dose.

3) Pharmacological Study

The pharmacological experiments to which the chemical molecules which are the subject of the present invention were subjected enabled a valuable activity on the cardiovascular system to be shown in both in vivo and in vitro tests. The compounds of general formula I proved capable of reducing the aggregant and vasoconstrictive effects of compound U.46619 at remarkably low doses.

a) In vitro action:

Blood is taken from white male New Zealand rabbits which have not received any treatment capable of disrupting the platelet functions.

After having allowed the first drops to flow freely, the blood is collected in plastic tubes containing 3.8% (wt/v) trisodium citrate 5.5 H$_2$O, the citrate/blood ratio being 1 volume of citrate per 9 volumes of blood.

The blood platelet aggregation study is carried out starting from plasmas rich in platelets obtained by centrifuging the above blood samples at low speed. It is measured with the aid of a Mustard aggregometer at a wavelength of 609 nm with a stirring speed of 1,100 revolutions/min.

The products to be studied are dissolved in polyethylene glycol 300 and pre-incubated for 1 min at 37° C. under a volume of 10 microliters, in a mixture of 300 microliters of plasma rich in platelets and 90 microliters of Tyrode's solution without calcium, pH=7.4. (Corresponding controls are produced by pre-incubating the vehicle on its own instead of solutions of products to be studied).

The blood platelet aggregation is initiated by the addition either of U.46619 (final concentrations: 1.05 to 2.44 micromoles) or of arachidonic acid (final concentrations: 50 to 100 micromoles).

Starting from the parameter of the maximum percentage aggregation, the anti-aggregant activity of a product is calculated using the formula:

$$\left[ \frac{\frac{\text{Max aggregation}}{(\text{control})} - \frac{\text{Max aggregation}}{(\text{product})}}{\frac{\text{Max aggregation}}{(\text{control})}} \right] \times 100$$

One curve: anti-aggregant activity=f (final concentration) is plotted for each product and the 50% inhibitory concentration determined from the graph.

In the case of aggregation with U.46619, the $IC_{50}$ are given in Table I for compounds 1, 2, 3, 7 and 11 by way of non-limiting example:

TABLE I

| Compound | $IC_{50}$ |
|---|---|
| 1 | $6 \times 10^{-7}$ M |
| 2 | $5 \times 10^{-7}$ M |
| 3 | $5 \times 10^{-6}$ M |
| 7 | $5 \times 10^{-7}$ M |
| 11 | $2 \times 10^{-6}$ M |

The percentage inhibition of the aggregation with arachidonic acid is given in Table II for compounds 2 and 3 by way of non-limiting examples:

TABLE II

| Compound | Final concentration of compound studied | % inhibition of platelet aggregation |
|---|---|---|
| 2 | $10^{-4}$ M | −100% |
|   | $10^{-5}$ M | −79% |
|   | $5.10^{-6}$ M | −31% |
| 3 | $10^{-4}$ M | −86% |
|   | $5.10^{-5}$ M | −78% |
|   | $10^{-5}$ M | −7% | b) Ex vivo action: inhibition of anti-aggregant effects using U.46619 in rabbits.

Because of their powerful activity in vitro, the anti-aggregant effects ex vivo were studied in rabbits. The substances of general formula I, which are the subject of the present invention, are administered orally as a 1% suspension in carboxymethylcellulose to natural male New Zealand rabbits weighing 2.5 to 3 kg after going without nourishment for about 18 h. Blood samples were taken by cardiac puncture at time 0 and after 90 min. The aggregant U.46619 was used under the same conditions as above and the measurement of the aggregation was carried out using the same technique.

The results are expressed in Table III in terms of percentage inhibition of the maximum amplitude of the aggregation curve at $t=+90$ min relative to the control curve at $t=0$ and are given for compounds 2 and 3 by way of non-limiting example:

TABLE III

| Compounds I | dose mg/kg | % inhibition of aggregation |
|---|---|---|
| 2 | 5 | −64% |
|   | 10 | −98% |
| 3 | 5 | −43% |
|   | 10 | −74% |

3) Therapeutic Applications

Having regard for their pharmacological activity, the derivatives of the present invention can be used in human and animal therapy for the treatment of cardiovascular disorders. The compounds inhibit platelet aggregation and the vasoconstrictive effects due to an activation of thromboxane $A_2$ at the platelet and the vascular tissue level, acting by antagonism of its receptors on these cells. The compounds of the present invention are active on aggregation induced by collagen and arachidonic acid and to a lesser degree on that induced by PAF and ADP. These properties therefore make it possible to reduce myocardial ischaemia and, in particular, restenoses after angioplasty or after injection of streptokinase. Because of their good bioavailability by the oral route, they can be used to treat cerebral or peripheral (arteritic) ischaemias and atherosclerosis. These compounds also have a secondary indication in the treatment of asthma, bacteriemal shock and glomerulonephrites and in virus diseases and also enable the disemination of cancer cells to be combatted.

The compounds of the present invention are used to prepare medicaments which can be administered to warm-blooded animals or to man.

The administration can be effected orally, parenterally or rectally and each dose consists of an inert pharmaceutical adjuvant facilitating the preparation and the absorption of the medicament and of the active principle, which can be combined with another. These medicaments can be in the form of tablets, capsules, suspensions, emulsions, syrups, suppositories, solutions or analogous preparations. The active principle is administered in an average dose of between 0.5 and 25 mg/kg body weight.

Three preparations are given by way of non-limiting example. The ingredients, and others, can be introduced in other proportions without modifying the scope of the invention.

EXAMPLE 30

Injectable Solution

| | |
|---|---|
| 1 injection flask make of inactinic glass containing pulverulent sodium 5-(2-parachlorobenzenesulphonamido-acetyl)-2,3-dihydro-2-benzofurancarboxylate | 20 mg |
| 1 sealed ampoule containing an apyrogenic sterile solution of distilled water + NaCl q.s. a final isotonic solution of | 2 ml |

Extemporaneous preparation of the solution before injection.

EXAMPLE 31

Tablets

| | |
|---|---|
| 5-(2-parachlorobenzenesulphonamidoacetyl)-2,3-dihydro-2-benzofurancarboxylic acid | 100 mg |
| lactose | 60 mg |
| corn starch | 20 mg |
| polyvinylpyrrolidone | 18 mg |
| magnesium stearate | 2 mg |
| tablet weighing | 200 mg |

EXAMPLE 32

Suppositories

| | |
|---|---|
| 5-(2-parachlorobenzenesulphonamidoacetyl)-2,3-dihydro-2-benzofurancarboxylic acid | 100 mg |
| suppository base (cocoa butter) q.s. | 2.5 g | to be stored in the absence of light, heat and moisture.

We claim:

1. New sulphonamide derivatives of carbocyclic or benzo-heterocyclic acids of general formula I

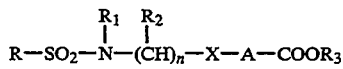

in which the radicals and substituents are defined as follows:

R represents a straight-chain or branched lower alkyl containing 1 to 9 carbon atoms, or phenyl or naphthyl radicals which are unsubstituted or substituted by one or more groups: lower alkyl (1 to 4 C), halogen, lower alkoxy (1 to 4 C), nitro, amino, dialkylamino or trifluoromethyl, or a thiophenyl radical;

$R_1$ represents hydrogen or a straight-chain or branched lower alkyl (1 to 4 C) or benzyl;

$R_2$ represents hydrogen or a straight-chain or branched lower alkyl (1 to 6 C), a phenyl group which is unsubstituted or substituted by a chlorine or a methoxy or an aralkyl group containing from 7 to 9 carbon atoms;

$R_3$ represents hydrogen or a straight-chain or branched lower alkyl (1 to 6 C);

—X— represents a divalent functional radical chosen from the following:

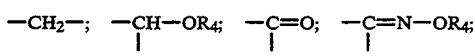

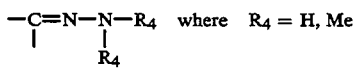

with the proviso, however, that X differs from —CH$_2$— when —A— represents divalent radicals a, b, d and e below, —A— represents a benzo-cyclic or benzo-heterocyclic divalent radical chosen from the following: (a–e) and (h–j)

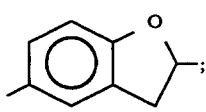 (a)

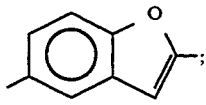 (b)

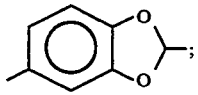 (c)

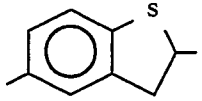 (d)

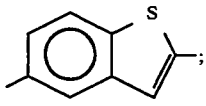 (e)

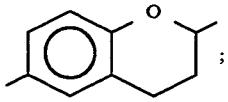 (g)

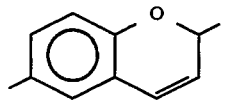 (h)

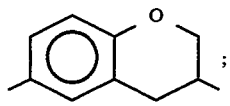 (i)

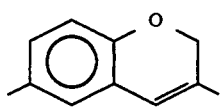 (j)

and n is 1 to 4 inclusive, the hydrated forms of acids of general formula I and the therapeutically acceptable organic or inorganic salts of I, it is being possible for the compounds of general formula I to be in the form of a racemic mixture or to be isolated in the form of enantiomers, diastereoisomers or their mixture in any proportions.

2. Compounds in accordance with claim 1 wherein X is —C=O.

3. Compounds in accordance with claim 1 wherein —A— is

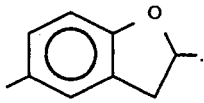

4. Compounds in accordance with claim 3 in which X is —C=O.

5. Compounds in accordance with claim 3 wherein R is a 4-chlorophenyl radical.

6. Compounds in accordance with claim 1 wherein X is —CH$_2$—.

7. Compounds in accordance with formula I of claim 1 wherein R is a 4-chlorophenyl radical.

8. Compounds in accordance with claim 1 wherein X is C=O, A is (a), $R_1$ and $R_2$ are each hydrogen atoms and n is 1.

9. The sulphonamide derivative of claim 1 where the therapeutically acceptable organic or inorganic salt is selected from the group consisting of sodium, calcium, zinc, 2-hydroxyethylammonium, bis(2-hydroxyethyl)ammonium, tris(2-hydroxyethyl)ammonium and morpholinium.

10. Compound according to claim 1, characterized in that it is chosen from the following compounds:

5-(parachlorobenzenesulphonamidoacetyl)-2,3-dihydro-2-benzofurancarboxylic acid 5-(2-parachlorobenzenesulphonamido-1-hydroxyethyl)-2,3-dihydro-2-benzofurancarboxylic acid 5-(2-parachlorobenzenesulphonamido-1-hydroxyiminoethyl)-2,3-dihydro-2-benzofurancarboxylic acid 5-(2-parachlorobenzenesulphonamido-1-methoxyiminoethyl)-2,3-dihydro-2-benzofurancarboxylic acid 5-(N-methyl-parachlorobenzenesulphonamidoacetyl)-2,3-dihydro-2-benzofurancarboxylic acid 5-(α-methyl-parachlorobenzenesulphonamidoacetyl)-2,3-dihydro-2-benzofurancarboxylic acid 5-(2-parachlorobenzenesulphonamido-1-hydroxypropyl)-2,3-dihydro-2-benzofurancarboxylic acid ethyl-5-(parachlorobenzenesulphonamidoacetyl)-2,3-dihydro-2-benzofurancarboxylate 5-(2-parachlorobenzenesulphonamidoacetyl)-1,3-benzodioxole-2-carboxylic acid 6-(2-parachlorobenzenesulphonamidoethyl)-2-chromancarboxylic acid 6-(parachlorobenzenesulphonamidoacetyl)-2-chromancarboxylic acid ethyl-6-(parachlorobenzenesulphonamidoacetyl)-2-chromancarboxylate 5-(benzenesulphonamidoacetyl)-2,3-dihydro-2-benzofurancarboxylic acid 5-(paramethoxybenzenesulphonamidoacetyl)-2,3-dihydro-2-benzofurancarboxylic acid 5-(pentafluorobenzenesulphonamidoacetyl)-2,3-dihydro-2-benzofurancarboxylic acid lysine 5-(parachlorobenzenesulphonamidoacetyl)-2,3-dihydro-2-benzofurancarboxylate lysine 6-(2-parachlorobenzenesulphonamidoethyl)-2-chromancarboxylate lysine 6-(parachlorobenzenesulphonamidoacetyl)-2-chromancarboxylate.

11. Pharmaceutical compositions characterized in that they contain, as active principle, at least one compound defined according to claims 1 or 10 in combination with an inert pharmaceutical carrier.

12. The method of treating a patient suffering from a disorder of the cardiovascular system which comprises administering to said patient an amount of at least one compound in accordance with claim 1 or 10 which is effective to inhibit thromboxane receptors.

13. Process for the preparation of chemical compounds according to claim 1 where A differs from b, e, h and j, characterized in that a benzo-cyclic or benzo-heterocyclic ester of formula II $$H-A-COOR_5 \quad\quad II$$

is reacted with a functional acyl halide of structure III

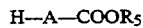
$$\underset{Y-(CH)_n-COY_1}{\overset{R_2}{|}} \quad\quad III$$

under Friedel-Crafts conditions using a compatible solvent in the presence of a Lewis acid and at a temperature varying from −5° C. to +50° C. so as to obtain the compound IVa of formula

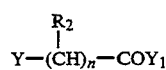
$$\underset{Y-(CH)_n-CO-A-COOR_5}{\overset{R_2}{|}} \quad\quad IVa$$

which itself is subjected to a condensation reaction with sodium nitride in an aqueous-alcoholic mixture at a temperature of between +10° C. and +50° C. to give the compound of formula:

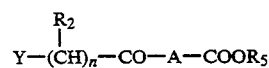
$$\underset{N_3-(CH)_n-CO-A-COOR_5}{\overset{R_2}{|}} \quad\quad V$$

which is selectively reduced by hydrogen in a lower alcohol containing an aqueous solution of a strong acid in the presence of a hydrogenation catalyst deposited on an inert support to give, at a temperature of between +10° C. and +50° C., the aminoketoester hydrochloride of formula VI:

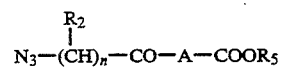
$$\underset{NH_2-(CH)_n-CO-A-COOR_5,\ HCl}{\overset{R_2}{|}} \quad\quad VI$$

which is itself subjected to a condensation reaction with a suitably substituted sulphonyl halide of formula:

$$R-SO_2Z \quad\quad VII$$

in a basic organic solvent at a temperature of between −15° C. and +40° C., to give the compound I where X=CO and $R_1$=H, and $R_3$ differs from H, of formula VIII:

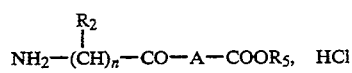
$$\underset{R-SO_2NH-(CH)_n-\overset{O}{\overset{\|}{C}}-A-COOR_5}{\overset{R_2}{|}} \quad\quad VIII$$

and, finally, this ester is saponified with an aqueous alkaline solution in the presence of a miscible organic solvent at a temperature of between +10° C. and the boiling point of the mixture, to give, after acidification, the acid compound I where X=CO, $R_1$=H and $R_3$=H, of formula IX

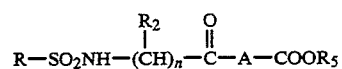
$$\underset{R-SO_2NH-(CH)_n-\overset{O}{\overset{\|}{C}}-A-COOR_3}{\overset{R_2}{|}} \quad\quad IX$$

and $R_5$=$R_3$ with the exception of H; Y and $Y_1$ represent a chlorine or a bromine and Z represents a fluorine or a chlorine or a bromine.

14. Process in accordance with claim 13 wherein said compatible solvent is methylene chloride or 1,2-dichloroethane, said Lewis acid is aluminum chloride, said strong acid is hydrochloric acid, said hydrogenation catalyst is palladium deposited on charcoal, said sulphonyl halide is a fluoride, chloride or bromide, said aqueous alkaline solution is a solution of sodium or potassium hydroxide, and said miscible organic solvent is selected from the group consisting of methanol, ethanol, dioxane and tetrahydrofuran.

15. Process for the preparation of chemical compounds according to claim 1 where A differs from b, e, h and j, characterized in that a benzo-carbocyclic or benzo-heterocyclic ester of general formula II $$H-A-COOR_5 \quad\quad II$$

is reacted with a functional acyl halide of structure IIIa

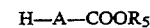
$$\underset{R_8OC-N-(CH)_n-COY}{\overset{O\ \ \ R_1\ R_2}{\overset{\|\ \ \ |\ \ \ |}{\ }}} \quad\quad IIIa$$

under Friedel-Crafts conditions using a compatible solvent in the presence of a Lewis acid and at a temperature of between −5° C. and +50° C. so as to obtain compound IVb of formula

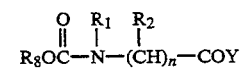
$$\underset{R_8OCON-(CH)_n-CO-A-COOR_5}{\overset{R_1\ R_2}{\overset{|\ \ \ |}{\ }}} \quad\quad IVb$$

which is itself reduced by an alkaline metal borohydride so as to obtain the derivative XXIX of formula $$R_8OCO-\underset{\underset{R_1}{|}}{N}-(CH)_n-\underset{\underset{R_2}{|}}{C}HOH-A-COOR_5 \quad \text{XXIX}$$

to lead, by basic hydrolysis, to the sodium salt of the aminohydroxy acid of formula XXX $$R_1NH-(CH)_n-\underset{\underset{R^2}{|}}{C}HOH-A-COOH \quad \text{XXX}$$

and finally, by subjecting a suitably substituted sulphonyl halide of formula $RSO_2Z$ to a condensation reaction with the crude sodium salt of XXX obtained above in the same aqueous-organic phase at a pH of between 11 and 13 and at a temperature of between 0° and +40° C., to give the compound I where $R_3=H$ and $X=CHOH$, of formula XXVII $$RSO_2\underset{\underset{R_1}{|}}{N}-(CH)_n-\underset{\underset{R_2}{|}}{C}HOH-A-COOH \quad \text{XXXVII}$$

in which the radicals in general formulae IVb, XXIX, XXX and XXVII are defined as follows:

R represents a straight-chain or branched lower alkyl containing 1 to 9 carbon atoms, or phenyl or naphthyl radicals that are unsubstituted or substituted with one or more lower alkyl containing 1 to 4 carbon atoms, halogen, lower alkoxy containing 1 to 4 carbon atoms, nitro, amino, dialkylamino, trifluoromethyl or a thiophenyl radical;

$R_1$ represents hydrogen or a straight-chain or branched lower alkyl containing 1 to 4 carbon atoms or benzyl;

$R_2$ represents hydrogen a straight-chain or branched lower alkyl containing 1 to 6 carbon atoms or a phenyl group which is unsubstituted or substituted by chlorine methoxy, or an aralkyl group containing 7 to 9 carbon atoms;

$R_3$ represents a straight-chain or branched lower alkyl containing 1 to 6 carbon atoms;

$R_5=R_3$ $R_8$ represents a straight-chain lower alkyl radical containing 1 to 6 carbon atoms;

n is 1 to 4 inclusive;

Y represents chlorine or bromine; and

Z represents fluorine, chlorine or bromine.

16. Process for the preparation of chemical compounds according to claim 1 where A differs from b, e, h and j, characterized in that a benzocyclic or benzoheterocyclic ester of formula II $$H-A-COOR_5 \quad \text{II}$$

is reacted with a functional acyl halide of structure III $$Y-(CH)_n-\underset{\underset{R_2}{|}}{C}OY_1 \quad \text{III}$$

under Friedel-Crafts conditions using a compatible solvent in the presence of a Lewis acid and at a temperature varying from −5° C. to +50° C. so as to obtain the compound IVa of formula $$Y-(CH)_n-\underset{\underset{R_2}{|}}{C}O-A-COOR_5 \quad \text{IVa}$$

which itself is subjected to a condensation reaction with sodium nitride in an aqueous-alcoholic mixture at a temperature of between +10° C. and +50° C. to give the compound of formula $$N_3-(CH)_n-\underset{\underset{R_2}{|}}{C}O-A-COOR_5 \quad \text{V}$$

which is reduced under an atmosphere of hydrogen in a lower alcohol containing an aqueous solution of a strong acid in the presence of a hydrogenation catalyst deposited on an inert support to give, at a temperature of between +10° C. and +60° C. and in the course of several hours to give the compound of formula XII $$NH_2-(CH)_n-\underset{\underset{R_2}{|}}{C}H-A-COOR_5 \quad \text{XII}$$
$$\phantom{NH_2-(CH)_n-}\overset{\overset{OH}{|}}{\phantom{C}}\phantom{H-A-COOR_5}$$

which is subjected to a condensation reaction with a suitably substituted sulfonyl halide of formula $$R-SO_2Z$$

in a basic organic solvent at a temperature of between −15° C. and +40° C., to give compound I wherein $X=CHOH$ and $R_1=H$ and $R_3$ differs from H, of formula XIII $$R-SO_2NH-(CH)_n-\underset{\underset{R_2}{|}}{C}H-A-COOR_5 \quad \text{XIII}$$

and finally this ester is saponified with an aqueous alkaline solution in the present of an alcoholic or ethereal miscible organic solvent at a temperature of between +10° C. and +60° C. to give, after acidification, the acid compound I where $X=CHOH$, $R_1=H$ and $R_3=H$, of formula XIV $$R-SO_2NH-(CH)_n-\underset{\underset{R_2}{|}}{C}H-A-COOR \quad \text{XIV}$$

wherein $R_3$ represents a straight-chain or branched lower alkyl containing 1 to 6 carbon atoms;

$R_5=R_3$;

Y and $Y_1$ independently represent chlorine or bromine;

Z represents fluorine, chlorine or bromine;

$R_2$ represents hydrogen, a straight-chain or branched lower alkyl containing 1 to 6 carbon atoms or a phenyl group which is unsubstituted or substituted by chlorine, methoxy or an aralkyl group containing 7 to 9 carbon atoms;

R represents a straight-chain or branched lower alkyl containing 1 to 9 carbon atoms, or phenyl or naphthyl radicals that are unsubstituted or substituted with one or more lower alkyl containing 1 to 4 carbon atoms, halogen, lower alkoxy containing 1 to 4 carbon atoms, nitro, amino, dialkylamino, trifluoromethyl or a thiophenyl radical; and n is 1 to 4 inclusive.

17. Process in accordance with claim 16 wherein said hydrogenation catalyst is palladium deposited on charcoal, said sulphonyl halide is a fluoride, chloride or bromide, said basic organic solvent is pyridine, said aqueous alkaline solution is sodium hydroxide or potassium hydroxide, said miscible organic solvent is selected from the group consisting of methanol, ethanol, dioxane and tetrahydrofuran, and wherein the progress of said reduction reaction is monitored by chromatography.

18. Process for the preparation of chemical compounds according to claim 1 where A differs from b, e, h and j, characterized in that a benzocyclic or benzo-heterocyclic ester of formula II

$$H\text{—}A\text{—}COOR_5 \qquad \text{II}$$

is reacted with a functional acyl halide of structure III

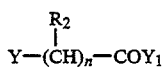

$$\underset{\underset{Y-(CH)_n-COY_1}{|}}{R_2} \qquad \text{III}$$

under Friedel-Crafts conditions using a compatible solvent in the presence of a Lewis acid and at a temperature varying from −5° C. to +50° C. so as to obtain the compound IVa of formula

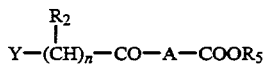

$$\underset{\underset{Y-(CH)_n-CO-A-COOR_5}{|}}{R_2} \qquad \text{IVa}$$

which itself is subjected to a condensation reaction with sodium nitride in an aqueous-alcoholic mixture at a temperature of between +10° C. and +50° C., to give the compound of formula V

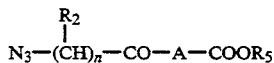

$$\underset{\underset{N_3-(CH)_n-CO-A-COOR_5}{|}}{R_2} \qquad \text{V}$$

which is selectively reduced by hydrogen in a lower alcohol containing an aqueous solution of a strong acid in the presence of a hydrogenation catalyst deposited on an inert support to give, at a temperature of between +10° C. and +50° C., the aminoketoester hydrochloride of formula VI

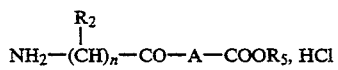

$$\underset{\underset{NH_2-(CH)_n-CO-A-COOR_5, \text{HCl}}{|}}{R_2} \qquad \text{VI}$$

which is reduced under excess hydrogen pressure in the presence of a strong acid using a hydrogenation catalyst in a carboxylic acid as the solvent carrying out the reaction at a temperature of between 20° C. and 90° C. under a hydrogen pressure of between 0.1 and 5 atmospheres to give the compound XV in the form of the base or the salt of formula

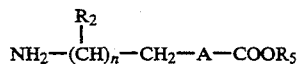

$$\underset{\underset{NH_2-(CH)_n-CH_2-A-COOR_5}{|}}{R_2} \qquad \text{XV}$$

which is then subjected to a condensation reaction with a sulfonyl halide to give the compound I where $R_1=H$ and $X=CH_2$, or formula XVI, a saturated homologue of VIII and XIII

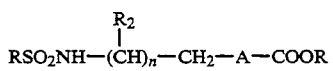

$$\underset{\underset{RSO_2NH-(CH)_n-CH_2-A-COOR}{|}}{R_2} \qquad \text{XVI}$$

which is saponified to prepare the derivatives IX and XIV, to give the compound I where $R_1=R_3+H$ and $X=CH_2$, of formula XVII

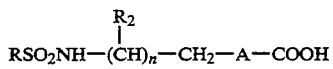

$$\underset{\underset{RSO_2NH-(CH)_n-CH_2-A-COOH}{|}}{R_2} \qquad \text{XVII}$$

wherein $R_3$ represents a straight-chain or branched lower alkyl containing 1 to 6 carbon atoms;

$R_5=R_3$;

Y and $Y_1$ independently represent chlorine or bromine;

n is 1 to 4 inclusive;

R represents a straight-chain or branched lower alkyl containing 1 to 9 carbon atoms, or phenyl or naphthyl radicals that are unsubstituted or substituted with one or more lower alkyl containing 1 to 4 carbon atoms, halogen, lower alkoxy containing 1 to 4 carbon atoms, nitro, amino, dialkylamino, trifluoromethyl or a thiophenyl radical; and $R_2$ represents hydrogen or a straight-chain or branched lower alkyl containing 1 to 6 carbon atoms or a phenyl group which is unsubstituted or substituted by chlorine, methoxy or an aralkyl group containing 7 to 9 carbon atoms.

19. Process according to claim 18 wherein said strong acid is sulphuric or perchloric acid.

20. Process for the preparation of chemical compounds according to claim 1 where A differs from b, e, h, and j, characterized in that a benzocyclic or benzo-heterocyclic ester of formula II $$H\text{—}A\text{—}COOR_5 \qquad \text{II}$$

is reacted with a functional acyl halide of structure III

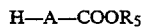

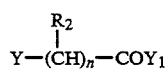

$$\underset{\underset{Y-(CH)_n-COY_1}{|}}{R_2} \qquad \text{III}$$

under Friedel-Crafts conditions using a compatible solvent in the presence of a Lewis acid and at a temperature varying from −5° C. to +50° C. so as to obtain the compound IVa of formula

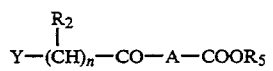

$$\underset{\underset{Y-(CH)_n-CO-A-COOR_5}{|}}{R_2} \qquad \text{IVa}$$

which is reduced to give the halogenated compound having the formula XIX

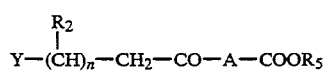

$$\underset{\underset{Y-(CH)_n-CH_2-CO-A-COOR_5}{|}}{R_2} \qquad \text{XIX}$$

which is subjected to a condensation reaction with the sodium salt, prepared in situ, of a suitably substituted secondary sulfonamide of formula XX

$$R\text{—}SO_2NH\text{—}R_7 \qquad \text{XX}$$

in an organic solvent at a temperature of between +5° C. and +60° C. to give the compound of formula XXI

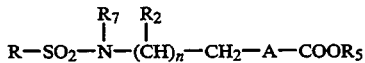
XXI which derivative is then saponified to give the equivalent saturated compound I where $X=CH_2$ and $R_3=H$, of formula XXII

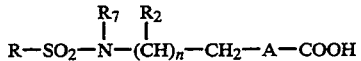
XXII and where $R_7$ represents either the radical $R_1$ other than hydrogen or the radical $R_6COO-$, where $R_6$ represents benzyl or a straight-chain or branched lower alkyl containing from 1 to 6 atoms inclusive;

wherein $R_3$ represents a straight-chain or branched lower alkyl containing 1 to 6 carbon atoms; $R_5=R_3$;

Y and $Y_1$ independently represent chlorine or bromine;

$R_2$ represents hydrogen or a straight-chain or branched lower alkyl containing 1 to 6 carbon atoms or a phenyl group which is unsubstituted or substituted by chlorine, methoxy or an aralkyl group containing 7 to 9 carbon atoms;

n is 1 to 4 inclusive; and

R represents a straight-chain or branched lower alkyl containing 1 to 9 carbon atoms, or phenyl or naphthyl radicals that are unsubstituted or substituted with one or more lower alkyl containing 1 to 4 carbon atoms, halogen, lower alkoxy containing 1 to 4 carbon atoms, nitro, amino, dialkylamino, trifluoromethyl or a thiophenyl radical.

21. Process according to claim 20 wherein said organic solvent is selected from the group consisting of dimethylformamide, dimethylacetamide, acetone, butanone, tetrahydrofuran and dioxane and $R_6$ is selected from methyl, ethyl and tert.-butyl radicals.

22. Process for the preparation of chemical compounds according to claim 1 where A differs from b, e, h and j, characterized in that a benzo-cyclic or benzo-heterocyclic ester of formula II

II is reacted with a functional acyl halide of structure III

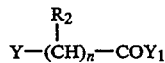
III under Friedel-Crafts conditions using a compatible solvent in the presence of a Lewis acid and at a temperature varying for $-5°$ C. to $+50°$ C. so as to obtain the compound IVa of formula

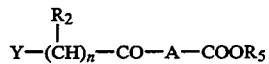
IVa which is reduced to give the halogenated compound having the formula XIX

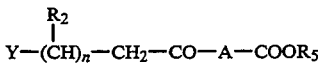
XIX which is subjected to a condensation reaction with the sodium salt, prepared in situ, of a suitably substituted secondary sulfonamide of formula XX

XX prepared in situ by the same process as to prepare compound XXI to give the ketosulhpamidoester I where $X=CO$, of formula XXIV

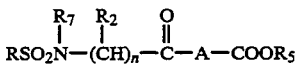
XXIV which is saponified to give the compound XXV where $R_1=H$ and $R_5=R_3$ and differs from H, which is then saponified to the acid as above, to give the compound I where $R_1=R_3=H$ and $X=CO$, of formula XXV

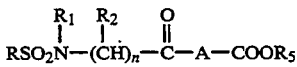
XXV wherein $R_3$ represents a straight-chain or branched lower alkyl containing 1 to 6 carbon atoms; $R_5=R_3$;

$R_7$ is $R_1$ other than H or the radical $R_6$ COO—;

$R_6$ represents benzyl or a straight-chain or branched chain lower alkyl containing 1 to 6 carbon atoms;

Y and $Y_1$ independently represent chlorine or bromine;

n is 1 to 4 inclusive;

$R_2$ represents hydrogen or a straight-chain or branched lower alkyl containing 1 to 6 carbon atoms or a phenyl group which is unsubstituted or substituted by chlorine, methoxy or an aralkyl group containing 7 to 9 carbon atoms; and R represents a straight-chain or branched lower alkyl containing 1 to 9 carbon atoms, or phenyl or naphthyl radicals that are unsubstituted or substituted with one or more lower alkyl containing 1 to 4 carbon atoms, halogen, lower alkoxy containing 1 to 4 carbon atoms, nitro, amino, dialkylamino, trifluoromethyl or a thiophenyl radical.

23. Process according to claim 22 wherein $R_7$ differs from $COOR_6$ and said saponification of the compound of formula XXIV is a direct saponification to give the compound I where X is CO, $R_3$ is H and $R_1$ differs from H.

24. Process according to claim 22 wherein $R_7$ is COO-tBu and said saponification of the compound of formula XXIV is preceded by a cleavage of the group $R_7$ in a strong acid medium to give compound XXV where $R_1$ is H, $R_5$ is the same as $R_3$ and differs from H.

25. Process according to claim 24 in which a crude mixture obtained after said condensation reaction is hydrolyzed by pouring it into a concentrated solution of a strong acid, heating at a temperature from about 40° to about 100° C. to give the compound I where $R_1$ is $R_3$ is hydrogen.

26. Process according to claim 25 in which said strong acid is hydrochloric acid and said temperature is between about 50° and 70° C.

27. Process for the preparation of chemical compounds according to claim 1 wherein A differs from b, e, h and j, characterized in that a benzo-cyclic or benzo-heterocyclic ester of formula II $$H-A-COOR_5 \qquad II$$

is reacted with a functional acyl halide of structure III $$\underset{|}{\overset{R_2}{Y-(CH)_n-COY_1}} \qquad III$$

under Friedel-Crafts conditions using a compatible solvent in the presence of a Lewis acid and at a temperature varying from $-5°$ C. to $+50°$ C. so as to obtain the compound IVa of formula $$\underset{|}{\overset{R_2}{Y-(CH)_n-CO-A-COOR_5}} \qquad IVa$$

which is reduced to give the halogenated compound having the formula XIX $$\underset{|}{\overset{R_2}{Y-(CH)_n-CH_2-CO-A-COOR_5}} \qquad XIX$$

which is subjected to a condensation reaction with the sodium salt, prepared in situ, of a suitably substituted secondary sulfonamide of formula XX $$R-SO_2NH-R_7 \qquad XX$$

to give the ketosulphamidoester I where X=CO, of formula XXIV $$\overset{R_7}{\underset{|}{R SO_2 N}}-\overset{R_2}{\underset{|}{(CH)_n}}-\overset{O}{\underset{||}{C}}-A-COOR_5 \qquad XXIV$$

which is reduced to give the sulfonamide homologue of formula XXI $$\overset{R_7}{\underset{|}{R-SO_2-N}}-\overset{R_2}{\underset{|}{(CH)_n}}-CH_2-A-COOR_5 \qquad XXI$$

and saponified to the corresponding acid I where X=CH$_2$ and R$_3$=H, of formula XXII
wherein R$_3$ represents a straight-chain or branched lower alkyl containing 1 to 6 carbon atoms;
R$_5$=R$_3$;
Y and Y$_1$ independently represent chlorine or bromine;
n is 1 to 4 inclusive;
R$_2$ represents hydrogen or a straight-chain or branched lower alkyl containing 1 to 6 carbon atoms or a phenyl group which is unsubstituted or substituted by chlorine, methoxy or an aralkyl group containing 7 to 9 carbon atoms;
R represents a straight-chain or branched lower alkyl containing 1 to 9 carbon atoms, or phenyl or naphthyl radicals that are unsubstituted or substituted with one or more lower alkyl containing 1 to 4 carbon atoms, halogen, lower alkoxy containing 1 to 4 carbon atoms, nitro, amino, dialkylamino, trifluoromethyl or a thiophenyl radical;
R$_7$ is R$_1$ other than H or the radical R$_6$ COO—; and
R$_1$ represents hydrogen or a straight-chain or branched lower alkyl containing 1 to 4 carbon atoms or benzyl.

28. Process according to claim 27 wherein said reduction step is under excess hydrogen pressure in the presence of a strong acid using a hydrogenation catalyst in a carboxylic acid as the solvent, carrying out the reaction at a temperature of between 20° and 90° C. under a hydrogen pressure of between 0.1 and 5 atmospheres.

29. Process according to claim 27 wherein said reduction step is by reducing compound VI with a trialkylsilane in the presence of trifluoroacetic acid at a temperature of between $+10°$ and $+40°$ C.

30. Process for the preparation of chemical compounds according to claim 1 where A differs from b, e, h, and j, characterized in that a benzo-cyclic or benzo-heterocyclic ester of formula II $$H-A-COOR_5 \qquad II$$

is reacted with a functional acyl halide of structure IIIa $$\overset{O}{\underset{||}{R_8OC}}-\overset{R_1}{\underset{|}{N}}-\overset{R_2}{\underset{|}{(CH)_n}}-COY \qquad IIIa$$

under Friedel-Crafts conditions using a compatible solvent in the presence of a Lewis acid and at a temperature of between $-5°$ C. and $+50°$ C. so as to obtain compound IVb of formula $$\overset{R_1}{\underset{|}{R_8OCON}}-\overset{R_2}{\underset{|}{(CH)_n}}-CO-A-COOR_5 \qquad IVb$$

is reduced to give a methylene group, to give the derivative XXXI of formula $$\overset{R_1}{\underset{|}{R_8OCON}}-\overset{R_2}{\underset{|}{(CH)_n}}-CH_2-A-COOR_5 \qquad XXXI$$

which is then saponified to lead to the sodium salt of the amino ester of formula XXXII $$\underset{|}{\overset{R_2}{R_1NH-(CH)_n-CH_2-A-COOH}} \qquad XXXII$$

which is condensed, without being isolated, with the sulfonyl halide of formula RSO$_2$Z to give, after acidification, the compound I where X=CO and R$_3$=H, of formula XXIII $$\overset{R_1}{\underset{|}{RSO_2N}}-\overset{R_2}{\underset{|}{(CH)_n}}-CH_2-A-COOH \qquad XXIII$$

wherein R$_3$ represents a straight-chain or branched lower alkyl containing 1 to 6 carbon atoms;
R$_5$=R$_3$;
Y represents chlorine or bromine;
Z represents fluorine, chlorine or bromine;

$R_1$ represents hydrogen or a straight-chain or branched lower alkyl containing 1 to 4 carbon atoms or benzyl;

$R_2$ represents hydrogen or a straight-chain or branched lower alkyl containing 1 to 6 carbon atoms or a phenyl group which is unsubstituted or substituted by chlorine, methoxy or an aralkyl group containing 7 to 9 carbon atoms;

n is 1 to 4 inclusive;

R represents a straight-chain or branched lower alkyl containing 1 to 9 carbon atoms, or phenyl or naphthyl radicals that are unsubstituted or substituted with one or more lower alkyl containing 1 to 4 carbon atoms, halogen, lower alkoxy containing 1 to 4 carbon atoms, nitro, amino, dialkylamino, trifluoromethyl or a thiophenyl radical; and $R_8$ represents a lower straight-chain alkyl radical containing 1 to 6 carbon atoms.

31. Process for the preparation of chemical compounds according to claim 1 where A differs from b, e, h and j, characterized in that a benzo-cyclic or benzo-heterocyclic ester of formula II

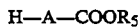  II

H—A—COOR$_5$ is reacted with a functional acyl halide of structure III

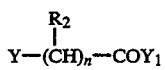  III $$Y-(CH)_n-COY_1$$

under Friedel-Crafts conditions using a compatible solvent in the presence of a Lewis acid and at a temperature varying from −5° C. to +50° C. so as to obtain the compound IVa of formula

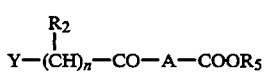  IVa $$Y-(CH)_n-CO-A-COOR_5$$

which itself is subjected to a condensation reaction with sodium nitride in an aqueous-alcoholic mixture at a temperature of between +10° C. and +50° C. to give the compound of formula

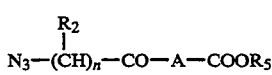  V $$N_3-(CH)_n-CO-A-COOR_5$$

which is selectively reduced by hydrogen in a lower alcohol containing an aqueous solution of a strong acid in the presence of a hydrogenation catalyst deposited on an inert support to give, at a temperature of between +10° C. and +50° C., the aminokestoester hydrochloride of formula VI

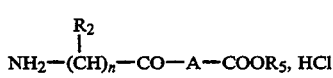  VI $$NH_2-(CH)_n-CO-A-COOR_5, HCl$$

is reduced by reducing compound VI with a trialkysilane in the presence of trifluoroacetic acid at a temperature of between +10° C. and +40° C. to give the compound XV in the form of the base or the salt of formula

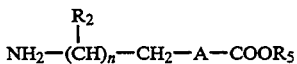  XV $$NH_2-(CH)_n-CH_2-A-COOR_5$$

which is then subjected to a condensation reaction with a sulfonyl halide to give the compound I where $R_1$=H and X=$CH_2$, or formula XVI, a saturated homologue of VIII and XIII

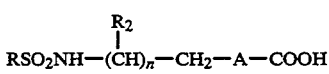  XVI $$RSO_2NH-(CH)_n-CH_2-A-COOH$$

which is saponified to prepare the derivatives IX and XIV, to give the compound I where $R_1$=$R_3$=H and X=$CH_2$, of formula XVII

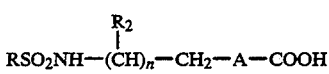  XVII $$RSO_2NH-(CH)_n-CH_2-A-COOH$$

wherein $R_3$ represents a straight-chain or branched lower alkyl containing 1 to 6 carbon atoms;

$R_5$=$R_3$;

Y and $Y_1$ independently represent chlorine or bromine;

$R_2$ represents hydrogen or a straight-chain or branched lower alkyl containing 1 to 6 carbon atoms or a phenyl group which is unsubstituted or substituted by chlorine, methoxy or an aralkyl group containing 7 to 9 carbon atoms;

R represents a straight-chain or branched lower alkyl containing 1 to 9 carbon atoms, or phenyl or naphthyl radicals that are unsubstituted or substituted with one or more lower alkyl containing 1 to 4 carbon atoms, halogen, lower alkoxy containing 1 to 4 carbon atoms, nitro, amino, dialkylamino, trifluoromethyl or a thiophenyl radical; and n is 1 to 4 inclusive.

32. Process in accordance with claim 31 in which said trialkylsilane is triethylsilane.

33. Process for the preparation of chemical compounds according to claim 1 where A differs from be, e, h and j, characterized in that a benzocyclic or benzo-heterocyclic ester of formula II

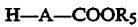  II

H—A—COOR$_5$ is reacted with a functional acyl halide of structure III

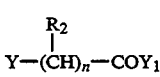  III $$Y-(CH)_n-COY_1$$

under Friedel-Crafts conditions using a compatible solvent in the presence of a Lewis acid and at a temperature varying from −5° C. to +50° C. so as to obtain the compound IVa of formula

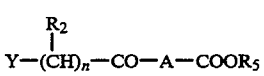  IVa $$Y-(CH)_n-CO-A-COOR_5$$

which itself is subjected to a condensation reaction with sodium nitride in an aqueous-alcoholic mixture at a temperature of between +10° C. and +50° C. to give the compound of formula

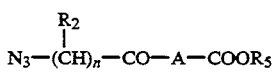

which is selectively reduced by hydrogen in a lower alcohol containing an aqueous solution of a strong acid in the presence of a hydrogenation catalyst deposited on an inert support to give, at a temperature of between +10° C. and +50° C., the aminoketoester hydrochloride of formula VI

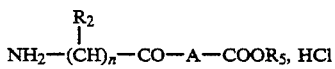

which is itself subjected to a condensation reaction with a suitably substituted sulfonyl halide of formula

in a basic organic solvent at a temperature of between −15° C. and +40° C., to give the compound I where $X=CO$ and $R_1=H$, and $R_3$ differs from H, of formula VIII

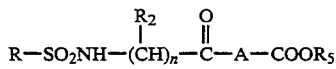

and, finally, this ester is saponified with an aqueous alkaline solution in the presence of a miscible organic solvent;

wherein $R_3$ represents a straight-chain or branched lower alkyl containing 1 to 6 carbon atoms;

$R_5 = R_3$;

Y and $Y_1$ independently represent chloride or bromine;

Z represents fluorine, chlorine or bromine;

$R_2$ represents hydrogen or a straight-chain or branched lower alkyl containing 1 to 6 carbon atoms or a phenyl group which is unsubstituted or substituted by chlorine, methoxy or an aralkyl group containing 7 to 9 carbon atoms;

R represents a straight-chain or branched lower alkyl containing 1 to 9 carbon atoms, or phenyl or naphthyl radicals that are unsubstituted or substituted with one or more lower alkyl containing 1 to 4 carbon atoms, halogen, lower alkoxy containing 1 to 4 carbon atoms, nitro, amino, dialkylamino, trifluoromethtyl or a thiophenyl radical; and n is 1 to 4 inclusive.

* * * * *